(12) United States Patent
Yoshinaga et al.

(10) Patent No.: US 10,506,919 B2
(45) Date of Patent: Dec. 17, 2019

(54) OPERATION SWITCHING MECHANISM AND ENDOSCOPE

(71) Applicant: OLYMPUS CORPORATION, Tokyo (JP)

(72) Inventors: Takuto Yoshinaga, Hachioji (JP); Kazuhiko Hino, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/619,618

(22) Filed: Jun. 12, 2017

(65) Prior Publication Data
US 2017/0273540 A1 Sep. 28, 2017

Related U.S. Application Data

(63) Continuation of application No. PCT/JP2016/055075, filed on Feb. 22, 2016.

(30) Foreign Application Priority Data

Mar. 6, 2015 (JP) .................................. 2015-044931

(51) Int. Cl.
 *A61B 1/00* (2006.01)
 *A61B 1/005* (2006.01)
(Continued)

(52) U.S. Cl.
CPC ........... *A61B 1/00188* (2013.01); *A61B 1/00* (2013.01); *A61B 1/00002* (2013.01);
(Continued)

(58) Field of Classification Search
CPC ............... G02B 23/24; G02B 23/2407; A61B 1/00002; A61B 1/00; A61B 1/00064;
(Continued)

(56) References Cited

U.S. PATENT DOCUMENTS

2004/0097791 A1* 5/2004 Tokuda .............. A61B 1/00183
  600/173
2007/0149855 A1* 6/2007 Noguchi ............ A61B 1/00096
  600/168

(Continued)

FOREIGN PATENT DOCUMENTS

EP   2 596 741 A1   5/2013
JP   2000-221415 A  8/2000
(Continued)

OTHER PUBLICATIONS

International Search Report dated May 24, 2016 issued in PCT/JP2016/055075.
(Continued)

*Primary Examiner* — Ryan N Henderson
*Assistant Examiner* — Pamela F Wu
(74) *Attorney, Agent, or Firm* — Scully, Scott, Murphy & Presser, P.C.

(57) ABSTRACT

An operation switching mechanism includes a wire, a reciprocating movement member, a first biasing member, a second biasing member, switching members configured to switch states in which the first biasing member and the second biasing member perform biasing, and an operation member configured to operate the switching members according to operation from an outside and move the reciprocating movement member to a first movement position or a second movement position.

13 Claims, 20 Drawing Sheets

(51) Int. Cl.
*G02B 23/24* (2006.01)
*G02B 23/26* (2006.01)

(52) U.S. Cl.
CPC .......... *A61B 1/0019* (2013.01); *A61B 1/0052* (2013.01); *A61B 1/00163* (2013.01); *G02B 23/24* (2013.01); *G02B 23/2407* (2013.01); *G02B 23/26* (2013.01); *A61B 1/00064* (2013.01); *A61B 1/00121* (2013.01)

(58) Field of Classification Search
CPC ... A61B 1/00121; A61B 1/005; A61B 1/0051; A61B 1/0052; A61B 1/0053; A61B 1/0055; A61B 1/0056; A61B 1/0057–0058; A61B 1/00068; A61B 1/00071; A61B 1/00128; A61B 1/00147; A61B 1/00188; A61B 1/0019; A61B 1/04; A61B 1/00163; A61B 1/00174; A61B 1/00177; A61B 1/00179; A61B 1/00181; A61B 1/00183; A61B 1/00186; A61B 1/00193; A61B 1/00195; A61B 1/00197; A61B 2017/003; A61B 2017/00305; A61B 2017/00314; A61B 2017/00318; A61B 2017/00323; A61B 2017/00327; A61B 2017/00313; A61B 2017/00336; A61B 2017/0034; A61B 2017/00367; A61B 2017/00371; A61B 2017/00376; A61B 2017/0038; A61B 2017/00384; A61B 2017/00389; A61B 2017/00393; A61B 2017/00398; A61M 25/0133; A61M 25/0136; A61M 25/0147; A61M 2025/015; A61M 2025/0163; A61M 25/0138; A61M 25/0141
USPC ................ 600/109, 111–112, 122, 125, 131, 600/136–142, 144–150, 160–168
See application file for complete search history.

(56) References Cited

U.S. PATENT DOCUMENTS

2013/0096384 A1* 4/2013 Arai ..................... A61B 1/0055
600/144
2015/0157187 A1* 6/2015 Cerveri .............. A61B 1/00188
600/118

FOREIGN PATENT DOCUMENTS

JP 2009-066222 A 4/2009
JP 2014-033716 A 2/2014

OTHER PUBLICATIONS

Extended Supplementary European Search Report dated Aug. 21, 2018 in European Patent Application No. 16 76 1466.8.

* cited by examiner

OPERATION SWITCHING MECHANISM AND ENDOSCOPE

CROSS REFERENCE TO RELATED APPLICATION

This application is a continuation application of PCT/JP2016/055075 filed on Feb. 22, 2016 and claims benefit of Japanese Application No. 2015-044931 filed in Japan on Mar. 6, 2015, the entire contents of which are incorporated herein by this reference.

BACKGROUND OF THE INVENTION

1. Field of the Invention

The present invention relates to an operation switching mechanism and an endoscope including a long member that transmits a force for operating an operating section.

2. Description of the Related Art

In recent years, endoscopes have been widely used in a medical field and an industrial field. With the endoscope used in the medical field, by inserting an elongated insertion section into a body cavity serving as a subject, it is possible to observe an organ in the body cavity with an optical system included in the insertion section and perform various kinds of treatment using, according to necessity, a treatment instrument inserted into an insert-through channel for the treatment instrument included in the endoscope.

With the endoscope used in the industrial field, by inserting an elongated insertion section of the endoscope into an object such as a jet engine or a pipe in a factory, it is possible to perform observation and inspection of scratches, corrosions, and the like of a site to be examined in the object with an optical system included in the insertion section.

A configuration is well known in which it is possible to change an observation magnification and a depth of field of a subject by reciprocatingly moving, using an operation switching mechanism, among optical members configuring an optical system provided in an insertion section of the endoscope, a zoom lens, which is an operating section, along an optical axis direction of the optical system.

More specifically, a configuration in which a known linear switch is used as the operation switching mechanism is well known. In the linear switch, a shape memory alloy for expanding to bias a zoom-lens holding frame, which holds a zoom lens, forward in an optical axis direction in a non-energized state and contracting to move the zoom-lens holding frame backward in the optical axis direction in an energized state is connected to the zoom-lens holding frame, whereby the linear switch reciprocatingly moves the zoom lens in the optical axis direction to be capable of being switched to two positions of a forward position and a backward position using the expansion and contraction of the shape memory alloy.

Note that examples of the forward position include a normal observation position at an equal magnification in the optical system and examples of the backward position include a near point magnifying observation position for performing a magnifying observation in the optical system.

Japanese Patent Application Laid-Open Publication No. 2000-221415 discloses a configuration of an operation switching mechanism in which a linear switch is used. The linear switch can reciprocatingly move a zoom lens frame, which holds a zoom lens in an insertion section of an endoscope, between a forward position and a backward position along a longitudinal direction of a wire substantially parallel to the optical axis direction and fix the zoom lens frame to be capable of being switched to the forward position and the backward position using two compression springs respectively wound in front and rear positions of the zoom lens frame around an outer circumference of a slide pin, which pierces through the zoom lens frame along an optical axis direction, and configured to respectively bias the zoom lens frame forward and backward in the optical axis direction and using the wire, which is a long member inserted through the insertion section of the endoscope, connected to the zoom lens frame, and towed and slacked using an operation member provided in an operation section of the endoscope.

SUMMARY OF THE INVENTION

An operation switching mechanism in an aspect of the present invention includes: a long member configured to transmit a force for operating an operating section; a reciprocating movement member to which the long member is connected, the reciprocating movement member reciprocatingly moving between a first movement position and a second movement position; a first biasing member configured to bias the reciprocating movement member toward the first movement position; a second biasing member configured to bias the reciprocating movement member toward the second movement position; a switching member configured to switch a state of the biasing by the first biasing member and the second biasing member such that the biasing by at least one of the first biasing member and the second biasing member is suppressed; and an operation member configured to operate the switching member according to operation from an outside and move the reciprocating movement member to the first movement position or the second movement position.

An endoscope according to an aspect of the present invention includes: an insertion section inserted into a subject; the operating section provided in the insertion section; and the operation switching mechanism configured to switch an operation state of the operating section.

DETAILED DESCRIPTION OF THE PREFERRED EMBODIMENT(S)

Embodiments of the present invention are explained below with reference to the drawings. Note that the drawings are schematic and relations between thicknesses and widths of respective members, ratios of the thicknesses of the respective members, and the like are different from real ones. It goes without saying that portions, relations and ratios of dimensions of which are different from one another, are included among the drawings.

(First Embodiment)

Figure 1:
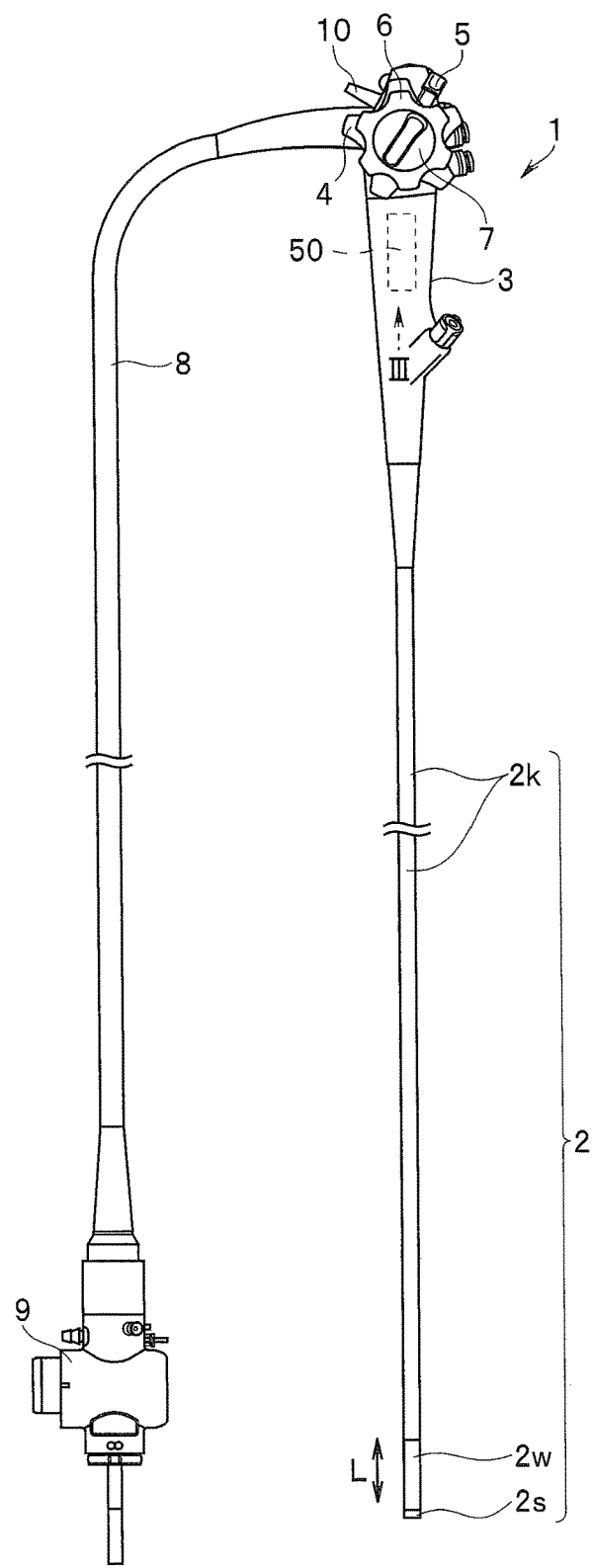
FIG. 1 is a perspective view showing an exterior of an endoscope including an operation switching mechanism of a first embodiment.
Figure 2A:
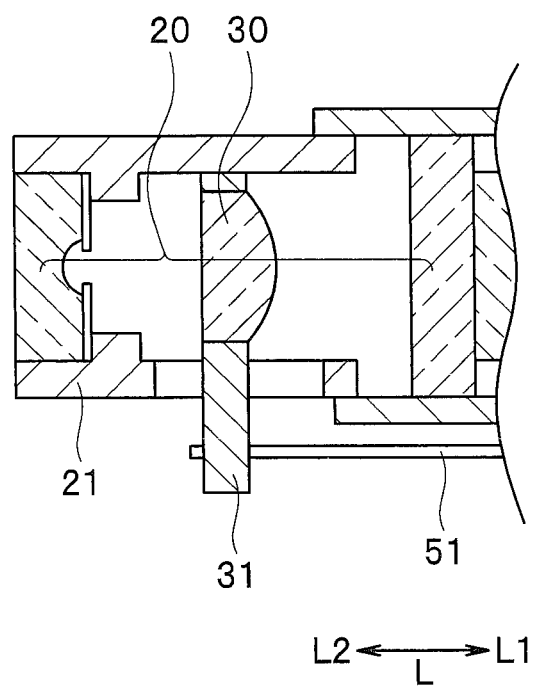
FIG. 2A is a partial sectional view showing an optical system, which is provided in a distal end portion of an insertion section of the endoscope shown in FIG. 1, together with a frame and a long member that hold the optical system.
Figure 2B:
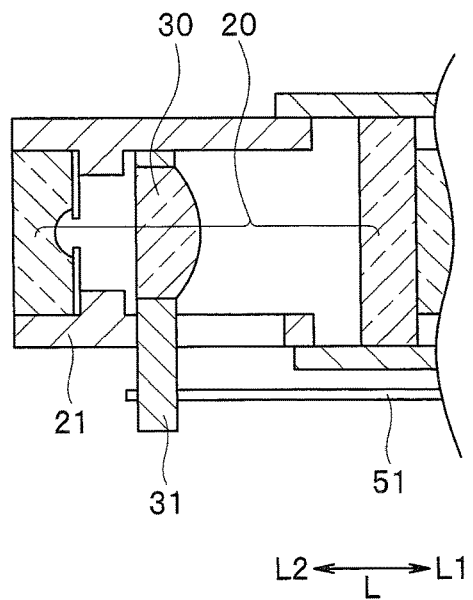
FIG. 2B is a partial sectional view showing a state in which an operating section shown in FIG. 2A moves forward in a longitudinal direction.
Figure 2C:
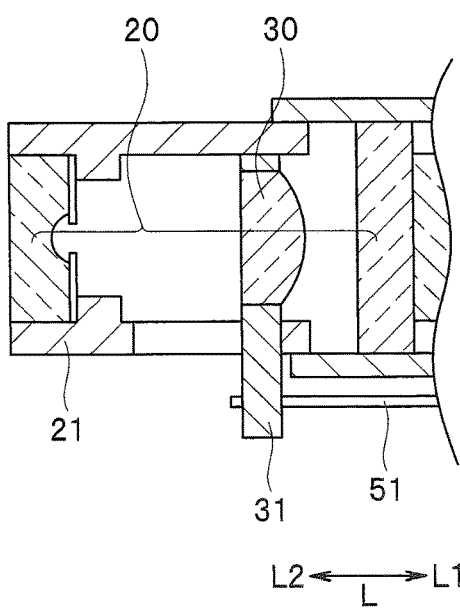
FIG. 2C is a partial sectional view showing a state in which the operating section shown in FIG. 2A moves backward in the longitudinal direction.

FIG. 1 is a perspective view showing an exterior of an endoscope including an operation switching mechanism of a first embodiment. FIG. 2A is a partial sectional view showing an optical system, which is provided in a distal end portion of an insertion section of the endoscope shown in FIG. 1, together with a frame and a long member that hold the optical system. FIG. 2B is a partial sectional view showing a state in which an operating section shown in FIG. 2A moves forward in a longitudinal direction. FIG. 2C is a partial sectional view showing a state in which the operating section shown in FIG. 2A moves backward in the longitudinal direction.

As shown in FIG. 1, a main part of an endoscope 1 includes an insertion section 2 inserted into a subject, an operation section 3 concatenated on a proximal end side of the insertion section 2, a universal cord 8 extended from the operation section 3, and a connector 9 provided at an extension end of the universal cord 8. Note that the endoscope 1 is electrically connected to external devices such as a control device and an illumination device via the connector 9.

In the operation section 3, an up-down bending operation knob 4 configured to bend a bending section 2w explained below of the insertion section 2 in an up-down direction and a left-right bending operation knob 6 configured to bend the bending section 2w in a left-right direction are provided.

In the operation section 3, a fixing lever 5 configured to fix a turning position of the up-down bending operation knob 4 and a fixing knob 7 configured to fix a turning position of the left-right bending operation knob 6 are provided.

Further, in the operation section 3, an operation switching mechanism 50 configured to switch an operation state of a zoom lens 30 explained below (see FIG. 2A) is provided and a zoom lever 10 configured to operate the operation switching mechanism 50 and switch the operation state of the zoom lens 30 to thereby adjust optical characteristics of an optical system 20 explained below (see FIG. 2A) is provided.

The insertion section 2 includes a distal end portion 2s, the bending section 2w, and a flexible tube section 2k in order from a distal end side along a longitudinal direction L of a wire 51 explained below (see FIG. 2A) substantially parallel to an optical axis direction of the optical system 20 explained below. The insertion section 2 is formed in an elongated shape.

The bending section 2w is bent, for example, in upward, downward, left, and right four directions by turning operation of the up-down bending operation knob 4 and the left-right bending operation knob 6 to thereby change an observation direction of the optical system 20 explained below provided in the distal end portion 2s and improve insertability of the distal end portion 2s in the subject. Further, the flexible tube section 2k is concatenated to a proximal end side of the bending section 2w.

An optical system 20 configured to observe an inside of the subject is provided in the distal end portion 2s concatenated to the distal end side of the bending section 2w.

As shown in FIG. 2A, the optical system 20 is configured from, for example, lenses, which are a plurality of optical members, and held in a lens frame 21.

Further, one optical member among the plurality of optical members configuring the optical system 20 configures a zoom lens 30, which is an operating section configured to reciprocatingly move along the longitudinal direction L to thereby adjust the optical characteristics of the optical system 20.

The zoom lens 30 is held in a zoom lens frame 31. In the zoom lens frame 31, a distal end of a wire 51, which is a long member configured to transmit a force for operating the zoom lens 30, is connected to a part extended further to an outer side in a radial direction of the optical system 20 than the lens frame 21.

Therefore, the wire 51 reciprocatingly moves forward and backward in the longitudinal direction L, whereby the zoom lens 30 reciprocatingly moves forward and backward in the longitudinal direction L as shown in FIGS. 2A and 2B via the zoom lens frame 31.

Note that the long member is not limited only to the wire 51 and only has to be a member that can transmit a force and a movement for reciprocating movement to the zoom lens 30, which is the operating section, from the operation switching mechanism 50 such as a filament that flexibly bends in a direction crossing the longitudinal direction L or a combination of the wire and the filament.

More specifically, the zoom lens 30 reciprocatingly moves between a forward position located forward in the longitudinal direction L and a backward position located backward in the longitudinal direction L.

Note that examples of the forward position include a normal observation position at an equal magnification in the optical system 20 and examples of the backward position include a near point magnifying observation position for performing a magnifying observation in the optical system 20.

That is, the wire 51 reciprocatingly moves the zoom lens 30 between the normal observation position and the near point magnifying observation position via the zoom lens frame 31 to thereby adjust the optical characteristics of the optical system 20.

Figure 3:
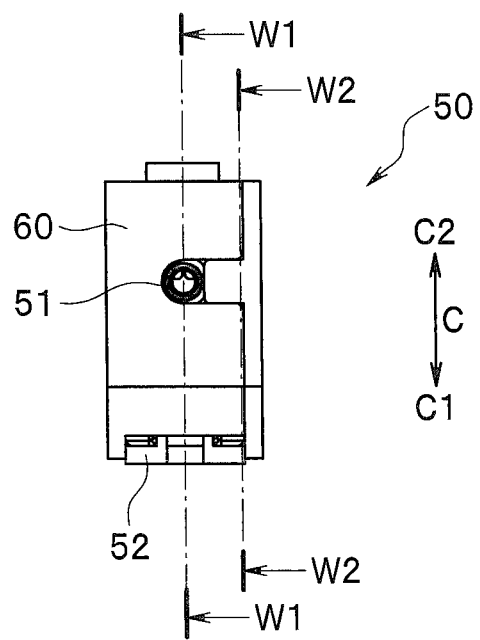
FIG. 3 is a plan view of the operation switching mechanism shown in FIG. 1 viewed from a III direction in FIG. 1.
Figure 4:
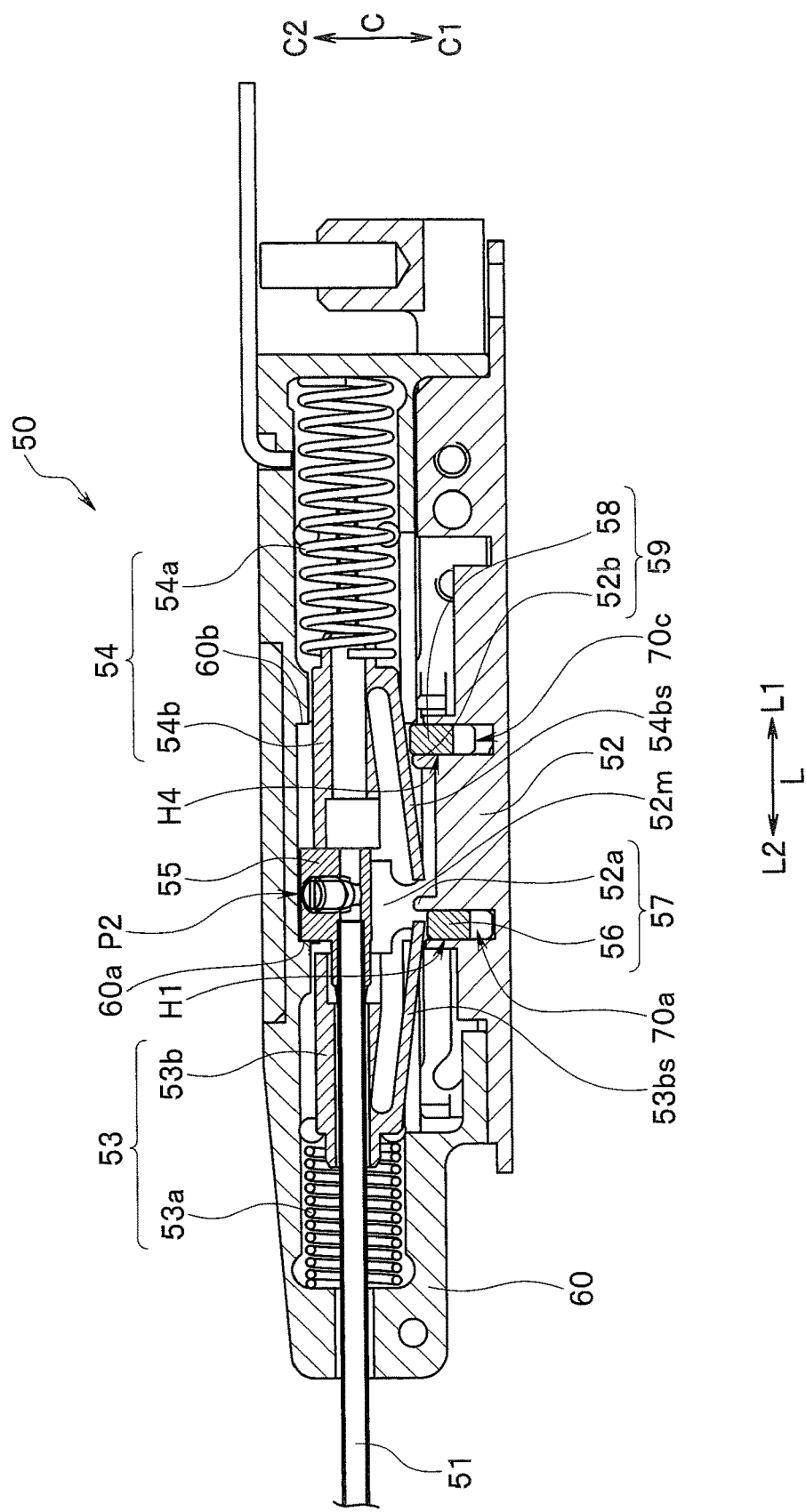
FIG. 4 is a partial sectional view of the operation switching mechanism along a W1-W1 line in FIG. 3 in a third state of an operation member in the operation switching mechanism shown in FIG. 3 and a state in which a reciprocating movement member is located in a second movement position.
Figure 5:
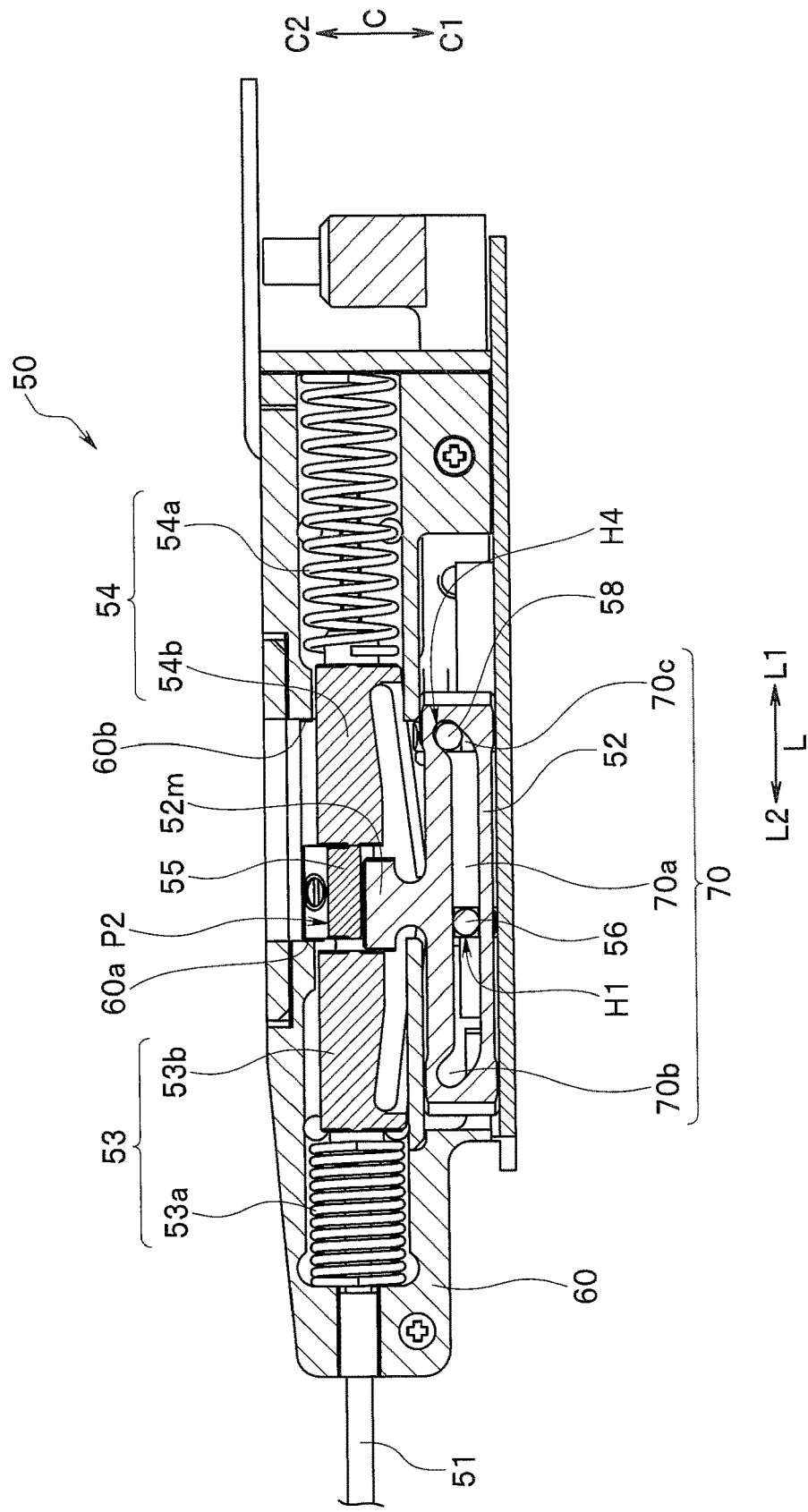
FIG. 5 is a partial sectional view of the operation switching mechanism along a W2-W2 line in FIG. 3 in the third state of the operation member in the operation switching mechanism shown in FIG. 3 and the state in which the reciprocating movement member is located in the second movement position.

A configuration of the operation switching mechanism 50 provided in the operation section 3 is explained with reference to FIG. 3 to FIG. 12. FIG. 3 is a plan view of the operation switching mechanism shown in FIG. 1 viewed from a III direction in FIG. 1. FIG. 4 is a partial sectional view of the operation switching mechanism along a W1-W1 line in FIG. 3 in a third state of an operation member in the operation switching mechanism shown in FIG. 3 and a state in which a reciprocating movement member is located in a second movement position. FIG. 5 is a partial sectional view of the operation switching mechanism along a W2-W2 line in FIG. 3 in the third state of the operation member in the operation switching mechanism shown in FIG. 3 and the state in which the reciprocating movement member is located in the second movement position.

Figure 6:
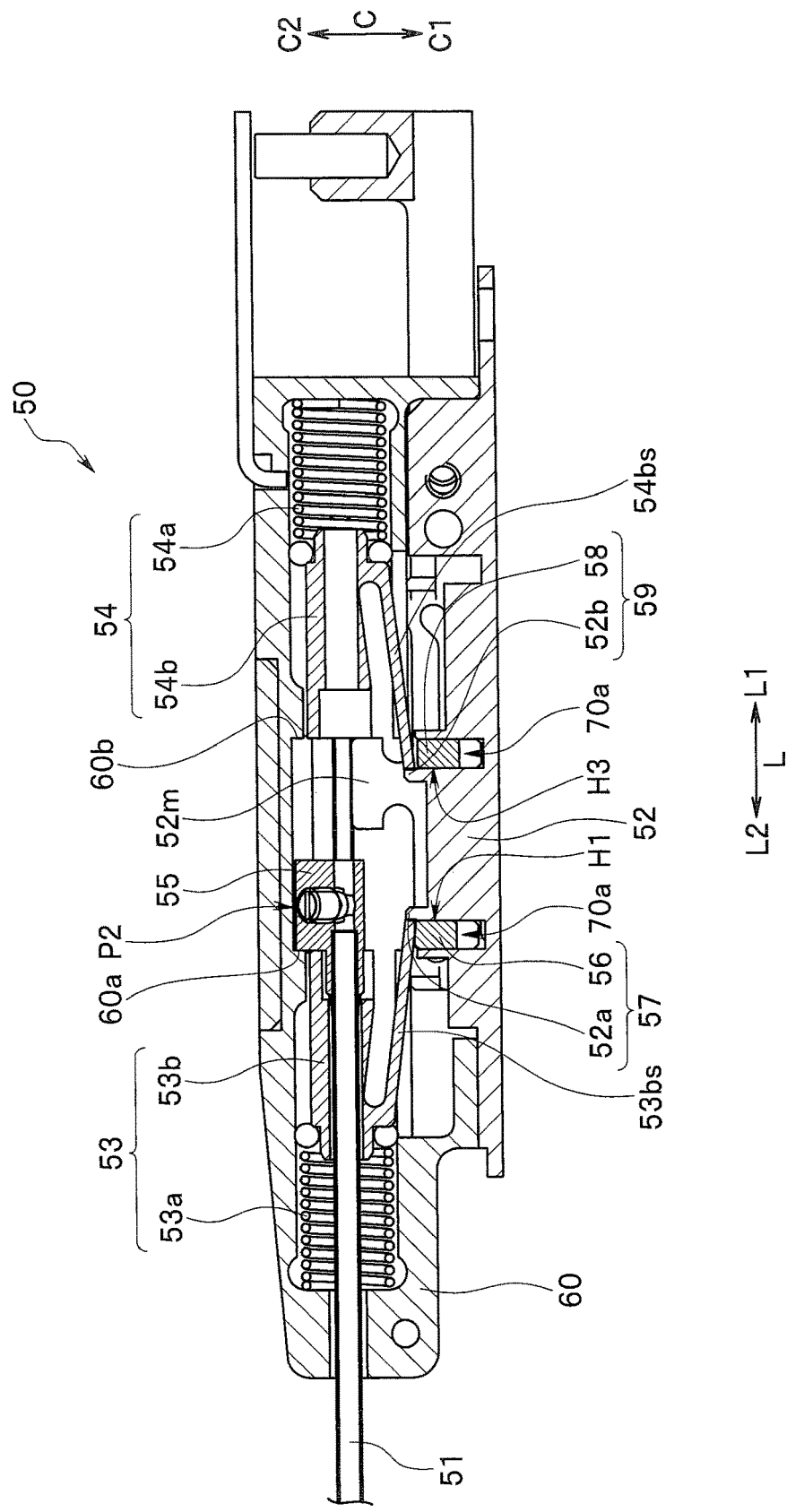
FIG. 6 is a partial sectional view of the operation switching mechanism along the W1-W1 line in FIG. 3 in a first state of the operation member in the operation switching mechanism shown in FIG. 3 and the state in which the reciprocating movement member is located in the second movement position.
Figure 7:
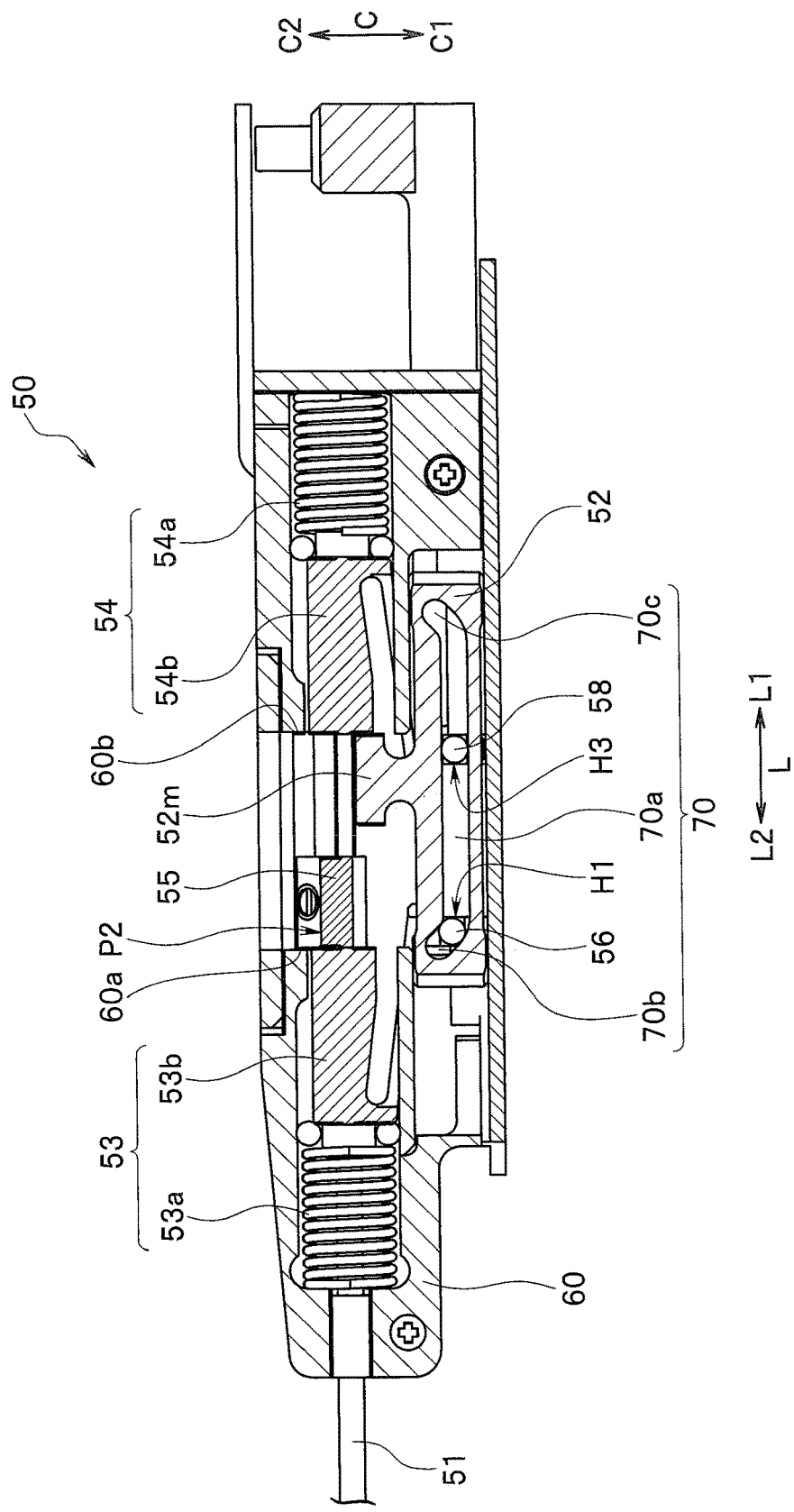
FIG. 7 is a partial sectional view of the operation switching mechanism along the W2-W2 line in FIG. 3 in the first state of the operation member in the operation switching mechanism shown in FIG. 3 and the state in which the reciprocating movement member is located in the second movement position.

FIG. 6 is a partial sectional view of the operation switching mechanism along the W1-W1 line in FIG. 3 in a first state of the operation member in the operation switching mechanism shown in FIG. 3 and the state in which the reciprocating movement member is located in the second movement position. FIG. 7 is a partial sectional view of the operation switching mechanism along the W2-W2 line in FIG. 3 in the first state of the operation member in the operation switching mechanism shown in FIG. 3 and the state in which the reciprocating movement member is located in the second movement position.

Figure 8:
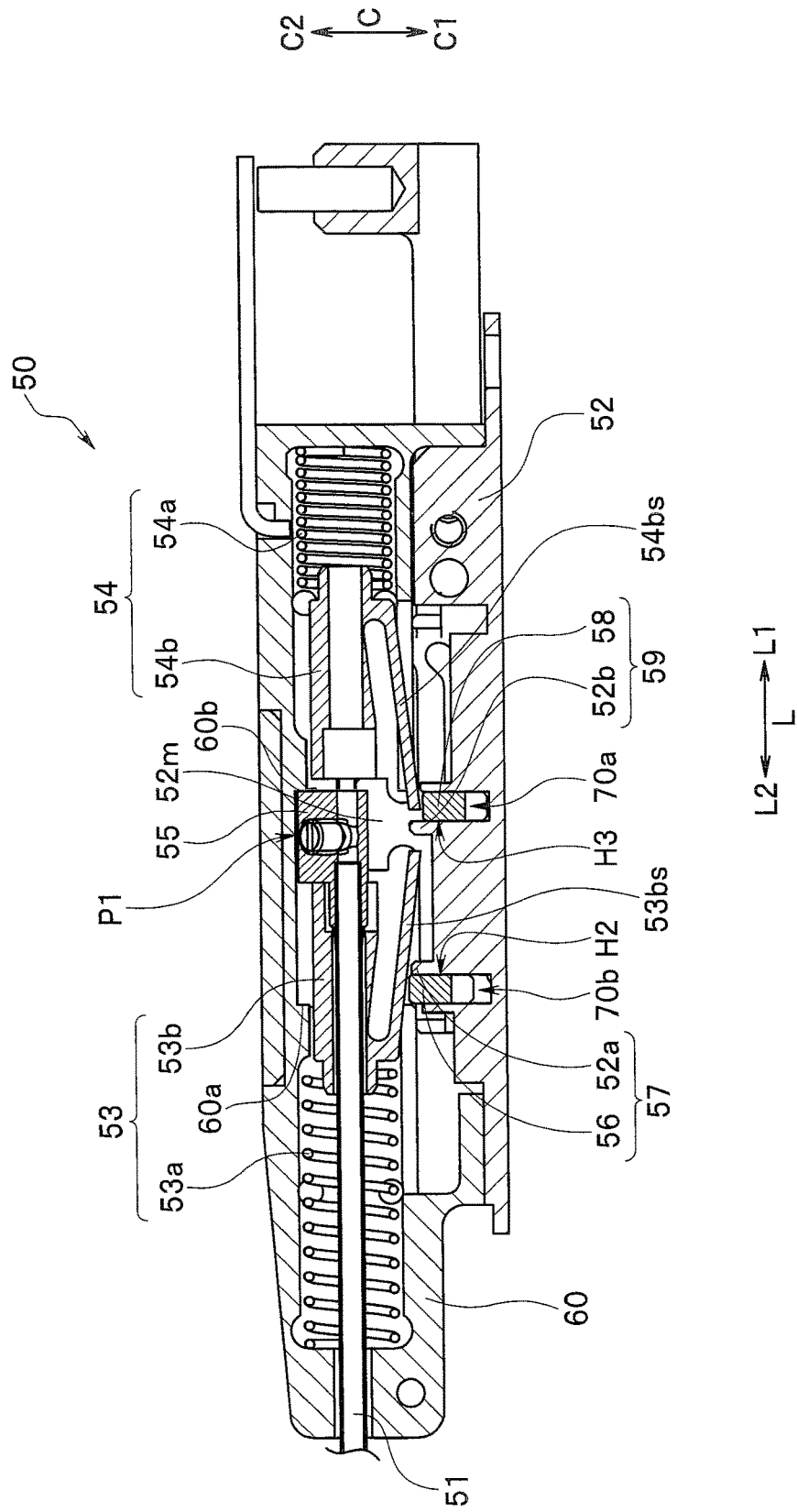
FIG. 8 is a partial sectional view of the operation switching mechanism along the W1-W1 line in FIG. 3 in a second state of the operation member in the operation switching mechanism shown in FIG. 3 and a state in which the reciprocating movement member is located in a first movement position.
Figure 9:
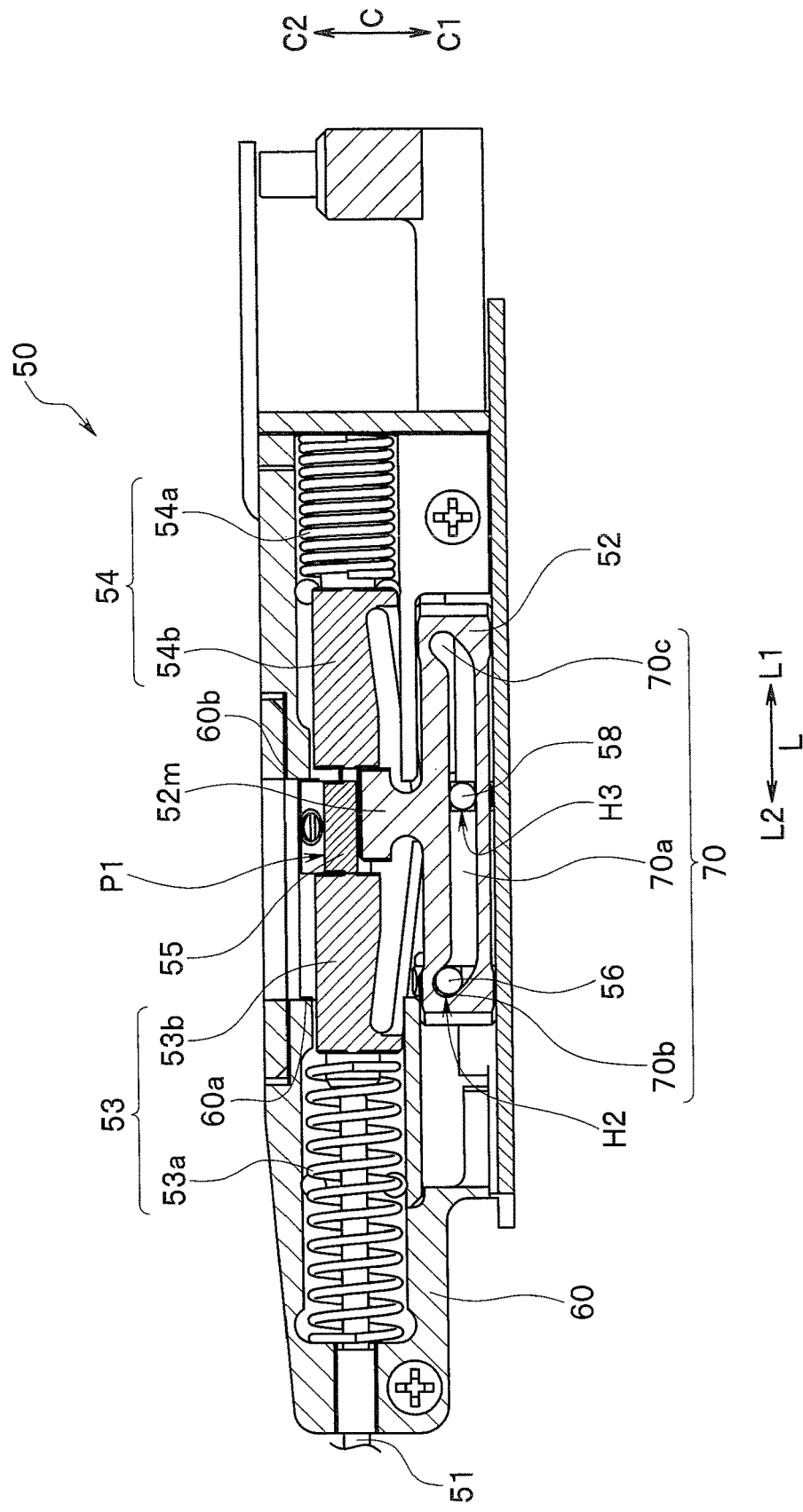
FIG. 9 is a partial sectional view of the operation switching mechanism along the W2-W2 line in FIG. 3 in the second state of the operation member in the operation switching mechanism shown in FIG. 3 and the state in which the reciprocating movement member is located in the first movement position.

Further, FIG. 8 is a partial sectional view of the operation switching mechanism along the W1-W1 line in FIG. 3 in a second state of the operation member in the operation switching mechanism shown in FIG. 3 and a state in which the reciprocating movement member is located in a first movement position. FIG. 9 is a partial sectional view of the operation switching mechanism along the W2-W2 line in FIG. 3 in the second state of the operation member in the operation switching mechanism shown in FIG. 3 and the state in which the reciprocating movement member is located in the first movement position.

Figure 10:
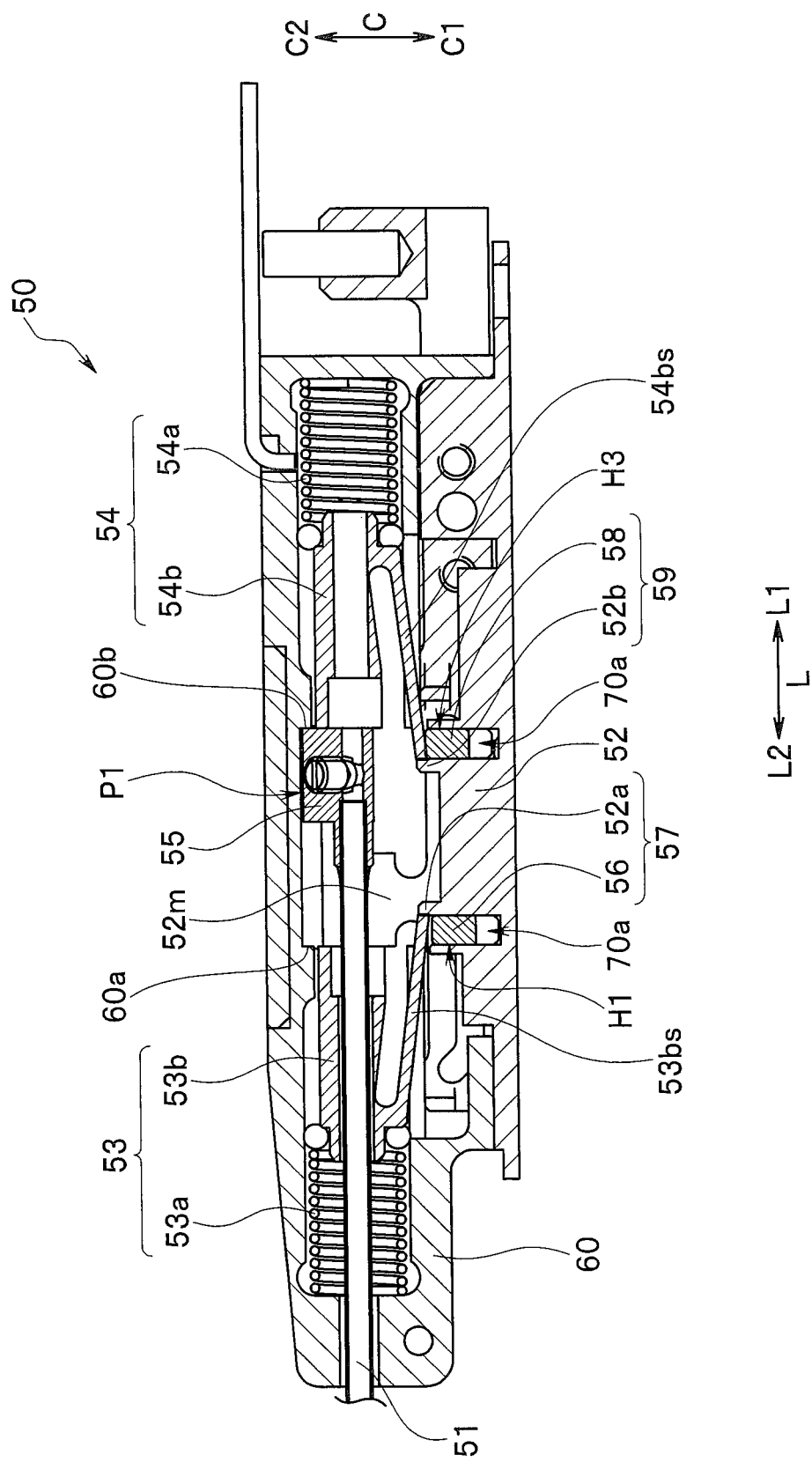
FIG. 10 is a partial sectional view of the operation switching mechanism along the W1-W1 line in FIG. 3 in the first state of the operation member in the operation switching mechanism shown in FIG. 3 and the state in which the reciprocating movement member is located in the first movement position.
Figure 11:
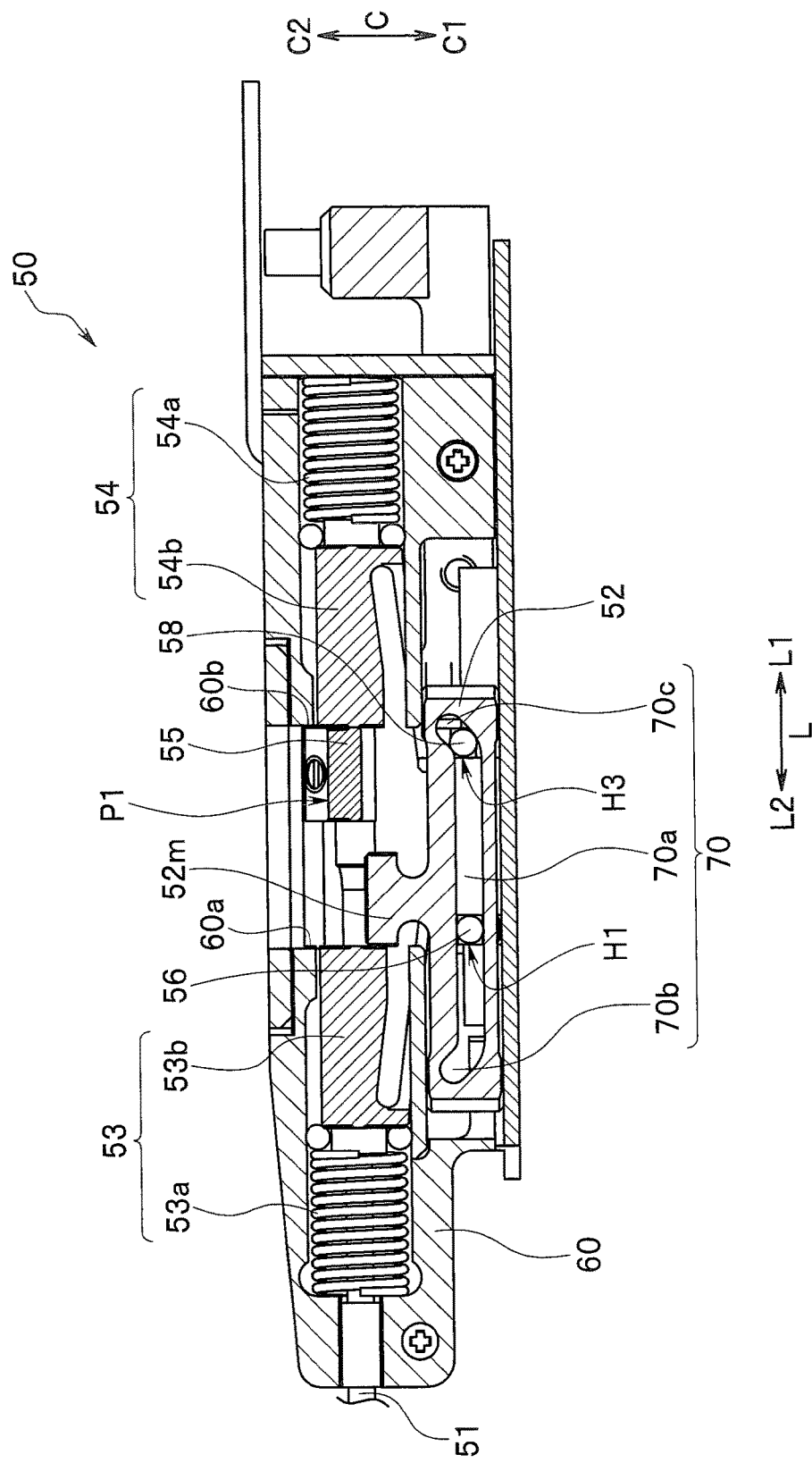
FIG. 11 is a partial sectional view of the operation switching mechanism along the W2-W2 line in FIG. 3 in the first state of the operation member in the operation switching mechanism shown in FIG. 3 and the state in which the reciprocating movement member is located in the first movement position.

FIG. 10 is a partial sectional view of the operation switching mechanism along the W1-W1 line in FIG. 3 in the first state of the operation member in the operation switching mechanism shown in FIG. 3 and the state in which the reciprocating movement member is located in the first movement position. FIG. 11 is a partial sectional view of the operation switching mechanism along the W2-W2 line in FIG. 3 in the first state of the operation member in the operation switching mechanism shown in FIG. 3 and the state in which the reciprocating movement member is located in the first movement position.

Figure 12:
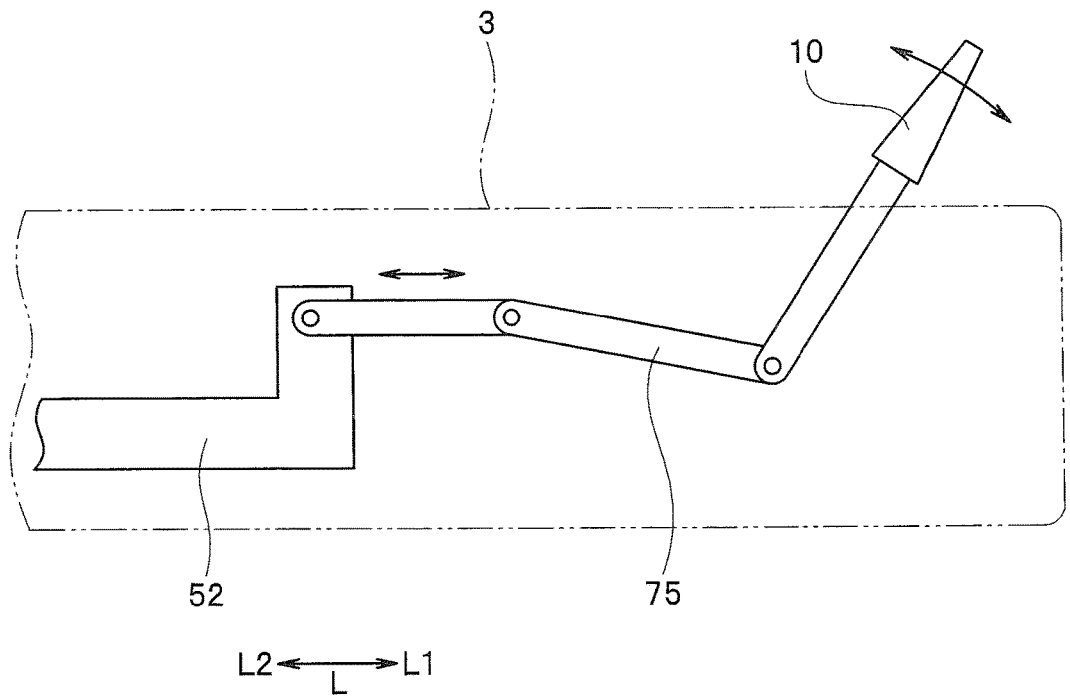
FIG. 12 is a diagram schematically showing a mechanism configured to reciprocatingly move the operation member in the operation switching mechanism shown in FIG. 3 via a zoom lever shown in FIG. 1.

Further, FIG. 12 is a diagram schematically showing a mechanism configured to reciprocatingly move the operation member in the operation switching mechanism shown in FIG. 3 via the zoom lever 10 shown in FIG. 1.

As shown in FIG. 3 to FIG. 11, a main part of the operation switching mechanism 50 includes an exterior housing 60, an operation member 52, a first biasing member 53, a second biasing member 54, a reciprocating movement member 55, a first switching member 57, and a second switching member 59 provided in the exterior housing 60, and the wire 51 extending from the exterior housing 60 to the insertion section 2 side serving as a front L2 side along the longitudinal direction L to an outside of the exterior housing 60.

As explained above, a distal end of the wire 51 is connected to the zoom lens frame 31. The wire 51 reciprocatingly moves to the front L2 side and a rear L1 side along the longitudinal direction L to thereby transmit a force for operating the zoom lens 30. The wire 51 is inserted through a biasing spring 53a explained below in the first biasing member 53.

A proximal end of the wire 51 is connected to the reciprocating movement member 55 in the exterior housing 60. The reciprocating movement member 55 reciprocatingly moves in the longitudinal direction L between a second movement position P2 shown in FIG. 4 to FIG. 7 where the reciprocating movement member 55 is in contact with a positioning protrusion 60a of the exterior housing 60 and a first movement position P1 shown in FIG. 8 to FIG. 11 where the reciprocating movement member 55 is in contact with a positioning protrusion 60b of the exterior housing 60.

Note that, when slight fluctuation of a stroke of sliding of the wire 51 due to a shape state of the insertion section 2 is anticipated, for example, the first movement position P1 is equivalent to a position switched to the backward position of the zoom lens 30 explained above, that is, the near point magnifying observation position of the optical system 20 as shown in FIG. 2C and the second movement position P2 is equivalent to a position switched to the forward position of the zoom lens 30 explained above, that is, the normal observation position of the optical system 20 as shown in FIG. 2B.

A main part of the first biasing member 53 is configured from a biasing spring 53a configured from an elastic member, a distal end of the biasing spring 53a being supported in the exterior housing 60, and a pressing member 53b provided at a proximal end of the biasing spring 53a and including a spring section 53bs. In the exterior housing 60, the first biasing member 53 biases the reciprocating movement member 55 to the rear L1 side, which is one side in the longitudinal direction L, serving as the first movement position P1.

The second biasing member 54 is located to be opposed to the first biasing member 53 in the longitudinal direction L. A main part of the second biasing member 54 is configured from a biasing spring 54a configured from an elastic member, a proximal end of the biasing spring 54a being supported in the exterior housing 60, and a pressing member 54b provided at a distal end of the biasing spring 54a and including a spring section 54bs. In the exterior housing 60, the second biasing member 54 biases the reciprocating movement member 55 to the front L2 side, which is the other side on an opposite side of the one side in the longitudinal direction L, serving as the second movement position P2.

The first switching member 57 and the second switching member 59 perform operation for switching suppression of biasing by the first biasing member 53 and release of suppression of biasing by the second biasing member 54 and release of the suppression of the biasing by the first biasing member 53 and the suppression of the biasing by the second biasing member 54.

More specifically, the first switching member 57 and the second switching member 59 perform switching operation for, after performing the suppression of the biasing by the first biasing member 53 and the suppression of the biasing by the second biasing member 54, releasing the suppression of the biasing by the second biasing member 54 while keeping suppressing the biasing by the first biasing member 53 or releasing the suppression of the biasing by the first biasing member 53 while keeping suppressing the biasing by the second biasing member 54.

That is, the first switching member 57 and the second switching member 59 are respectively operated, whereby states of the biasing by the first biasing member 53 and the second biasing member 54 are switched such that the biasing by at least one of the first biasing member 53 and the second biasing member 54 is suppressed.

More specifically, a main part of the first switching member 57 includes a protrusion 52a provided in the operation member 52 and a first moving member 56.

As shown in FIG. 4, FIG. 6, and FIG. 10, an end portion of the spring section 53bs is brought into contact with the protrusion 52a in a first position H1 explained below of the first moving member 56, whereby the protrusion 52a suppresses the biasing by the first biasing member 53.

As shown in FIG. 5, FIG. 7, FIG. 9, and FIG. 11, an end portion of the first moving member 56 fits in a cam groove 70 in the operation member 52. According to movement of the operation member 52 to the front L2 side and the rear L1 side in the longitudinal direction L, in the cam groove 70, the first moving member 56 reciprocatingly moves in a C1 direction and a C2 direction only in a direction C crossing the longitudinal direction L between a first position H1 for suppressing the biasing by the first biasing member 53 as shown in FIG. 5, FIG. 7, and FIG. 11 and a second position H2 for releasing the suppression of the biasing by the first biasing member 53 as shown in FIG. 9.

Note that, the first moving member 56 fits in a linear section 70a in the cam groove 70 in the first position H1 as shown in FIG. 5, FIG. 7, and FIG. 11 and fits in a key section 70b in the cam groove 70 in the second position H2 as shown in FIG. 9.

A main part of the second switching member 59 includes a protrusion 52b provided in the operation member 52 and a second moving member 58.

As shown in FIG. 6, FIG. 8, and FIG. 10, in a third position H3 explained below of the second moving member 58, a distal end of the spring section 54bs is brought into contact with the protrusion 52b, whereby the protrusion 52b suppresses the biasing by the second biasing member 54.

As shown in FIG. 5, FIG. 7, FIG. 9, and FIG. 11, an end portion of the second moving member 58 fits in the cam groove 70 in the operation member 52. According to movement of the operation member 52 to the front L2 side and the rear L1 side in the longitudinal direction L, in the cam groove 70, the second moving member 58 reciprocatingly moves in the C1 direction and the C2 direction only in the direction C between a third position H3 for suppressing the biasing by the second biasing member 54 as shown in FIG. 7, FIG. 9, and FIG. 11 and a fourth position H4 for releasing the suppression of the biasing by the second biasing member 54 as shown in FIG. 5.

The second moving member 58 fits in the linear section 70a in the cam groove 70 in the third position H3 as shown in FIG. 7, FIG. 9, and FIG. 11 and fits in a key section 70c in the cam groove 70 in the fourth position H4 as shown in FIG. 5.

The operation member 52 operates the first switching member 57 and the second switching member 59 and moves the reciprocating movement member 55 to the first movement position P1 or the second movement position P2 according to operation from the outside.

More specifically, as shown in FIG. 12, the operation member 52 is connected to the zoom lever 10 via a link mechanism 75. The operation member 52 is configured to be capable of reciprocatingly moving to the front L2 side and the rear L1 side in the longitudinal direction L via the link mechanism 75 according to turning of the zoom lever 10.

In the operation member 52, besides the protrusions 52a and 52b explained above, as shown in FIG. 5, FIG. 7, FIG. 9, and FIG. 11, the cam groove 70 including the linear section 70a having a predetermined length along the longitudinal direction L, the key section 70b bending from a distal end of the linear section 70a to the direction C2 side, and the key section 70c bending from a proximal end of the linear section 70a to the direction C2 side is formed. Further, a return member 52m located between the pressing member 53b and the pressing member 54b in the longitudinal direction L is formed.

The operation member 52 moves the first moving member 56 between the first position H1 and the second position H2 in the direction C or moves the second moving member 58 between the third position H3 and the fourth position H4 in the direction C using the cam groove 70.

More specifically, the operation member 52 can be switched to, according to the reciprocating movement in the longitudinal direction L, any one state of a first state for disposing the first moving member 56 in the first position H1 and disposing the second moving member 58 in the third position as shown in FIG. 6, FIG. 7, FIG. 10, and FIG. 11 to thereby locate the reciprocating movement member 55 in the first movement position P1 as shown in FIG. 10 and FIG. 11 or locate the reciprocating movement member 55 in the second movement position P2 as shown in FIG. 6 and FIG. 7, a second state for disposing the first moving member 56 in the second position H2 and disposing the second moving member 58 in the third position H3 as shown in FIG. 8 and FIG. 9 to locate the reciprocating movement member 55 in the first movement position P1 according to biasing to the rear L1 side by the first biasing member 53, and a third state for disposing the first moving member 56 in the first position H1 and disposing the second moving member 58 in the fourth position H4 as shown in FIG. 4 and FIG. 5 to thereby locate the reciprocating movement member 55 in the second movement position P2 according to biasing to the front L2 side by the second biasing member 54.

Note that, in the second state shown in FIG. 8 and FIG. 9, according to the biasing to the rear L1 side by the first biasing member 53, the reciprocating movement member 55 is pressed against the positioning protrusion 60*b* with a biasing force. Therefore, the reciprocating movement member 55 less easily moves from the first movement position P1.

Therefore, if a force equal to or larger than the biasing force of the first biasing member 53 is applied to the front L2 side, it is likely that the reciprocating movement member 55 moves to the front L2 side. In this case, a not-shown resisting section configured to apply a resistance force against the reciprocating movement member 55 moving forward from the first movement position P1 along the longitudinal direction L with a force equal to or larger than the biasing force of the first biasing member 53 only has to be provided in at least one of the reciprocating movement member 55 or the wire 51.

Note that examples of the resisting section include a friction member provided in a passing section of the wire 51 in the insertion section 2 and configured to apply a frictional force to the wire 51 and a mechanism configured to apply a frictional force to the reciprocating movement member 55 when the first moving member 56 comes into contact with a bottom surface of the reciprocating movement member 55 and the like.

In the third state shown in FIG. 4 and FIG. 5, the reciprocating movement member 55 is pressed against the positioning protrusion 60*a* with a biasing force according to the biasing to the front L2 side by the second biasing member 54. Therefore, the reciprocating movement member 55 less easily moves from the second movement position P2.

Therefore, if a force equal to or larger than the biasing force of the second biasing member 54 is applied to the rear L1 side, it is likely that the reciprocating movement member 55 moves to the rear L1 side. In this case, a not-shown resisting section configured to apply a resistance force against the reciprocating movement member 55 moving backward from the second movement position P2 along the longitudinal direction L with a force equal to or larger than the biasing force of the second biasing member 54 only has to be provided in at least one of the reciprocating movement member 55 or the wire 51.

Note that examples of the resisting section include a friction member provided in the passing section of the wire 51 in the insertion section 2 and configured to apply a frictional force to the wire 51 and a mechanism configured to apply a frictional force to the reciprocating movement member 55 when the second moving member 58 comes into contact with a bottom surface of the reciprocating movement member 55 and the like.

The return member 52*m* has a function of biasing the first biasing member 53 to the front L2 side and returning the first biasing member 53 to the first position H1 when the operation member 52 transitions from the second state shown in FIG. 8 and FIG. 9 to the first state shown in FIG. 10 and FIG. 11 and biasing the second biasing member 54 to the rear L1 side and returning the second biasing member 54 to the third position H3 when the operation member 52 transitions from the third state shown in FIG. 4 and FIG. 5 to the first state shown in FIG. 6 and FIG. 7.

Action of the operation switching mechanism 50 in the present embodiment configured in this way is explained.

First, in the operation member 52, when the reciprocating movement member 55 is located in the second movement position P2, which is the normal observation position of the zoom lens 30, as shown in FIG. 4 and FIG. 5, as explained above, according to the biasing to the front L2 side by the second biasing member 54, the reciprocating movement member 55 is pressed against the positioning protrusion 60*a* with a biasing force. Therefore, the reciprocating movement member 55 less easily moves from the second movement position P2.

Thereafter, when the operation member 52 transitions from the third state shown in FIG. 4 and FIG. 5 in which the operation member 52 is located in the second movement position P2 to the second state shown in FIG. 8 and FIG. 9 in which the reciprocating movement member is located in the first movement position P1, which is the near point magnifying observation position of the zoom lens 30, the operation member 52 is moved to the rear L1 side from the states in FIG. 4 and FIG. 5. First, the operation member 52 transitions from the third state shown in FIG. 4 and FIG. 5 to the first state shown in FIG. 6 and FIG. 7.

At this point, as shown in FIG. 5 and FIG. 7, the second moving member 58 moves from the fourth position H4 to the third position H3, that is, fits in the linear section 70*a* from the key section 70*c* in the cam groove 70. The first moving member 56 stays in the first position H1.

The return member 52*m* biases the second biasing member 54 to the rear L1 side and returns the second biasing member 54 to the third position H3. As a result, as shown in FIG. 6 and FIG. 7, a state in which the second biasing member 54 biases the reciprocating movement member 55 to the front L2 side is released. The biasing is suppressed by the second switching member 59.

The first biasing member 53 keeps a state in which the biasing is suppressed by the first switching member 57. Therefore, even if the operation member 52 transitions from the third state to the first state, the reciprocating movement member 55 remains located in the second movement position P2 as shown in FIG. 6 and FIG. 7.

Thereafter, the operation member 52 is moved further to the rear L1 side than in FIG. 6 and FIG. 7 to thereby transition from the first state shown in FIG. 6 and FIG. 7 to the second state shown in FIG. 8 and FIG. 9.

At this point, as shown in FIG. 7 and FIG. 9, the first moving member 56 moves from the first position H1 to the second position H2, that is, fits in the key section 70b from the linear section 70a in the cam groove 70. The second moving member 58 stays in the third position H3.

As a result, according to the fitting of the first moving member 56 in the key section 70b bending to the direction C2 side, as shown in FIG. 8 and FIG. 9, the first moving member 56 moves the spring section 53bs to the direction C2 side to a position where the spring section 53bs is not in contact with the protrusion 52a, whereby the first biasing member 53 biases the reciprocating movement member 55 to the rear L1 side.

Therefore, the reciprocating movement member 55 moves from the second movement position P2 to the first movement position P1 and is pressed against the positioning protrusion 60b with a biasing force by the first biasing member 53. In this case, the second biasing member 54 keeps the state in which the biasing is suppressed by the second switching member 59.

Consequently, the operation member 52 transitions from the third state to the second state. The zoom lens 30 moves backward via the reciprocating movement member 55, the wire 51, and the zoom lens frame 31 to thereby move from the normal observation position to the near point magnifying observation position.

Contact sound of the reciprocating movement member 55 coming into contact with the positioning protrusion 60b or release sound of the biasing spring 54a released from a contracted state occurs. Therefore, an operator can easily recognize that the zoom lens 30 moves from the normal observation position to the near point magnifying observation position.

In the operation member 52, when the reciprocating movement member 55 is located in the first movement position P1, which is the near point magnifying observation position of the zoom lens 30, as shown in FIG. 8 and FIG. 9, according to the biasing to the rear L1 side by the first biasing member 53, the reciprocating movement member 55 is pressed against the positioning protrusion 60b with a biasing force. Therefore, the reciprocating movement member 55 less easily moves from the first movement position P1.

Thereafter, when the operation member 52 transitions from the second state shown in FIG. 8 and FIG. 9 in which the operation member 52 is located in the first movement position P1 to the third state shown in FIG. 4 and FIG. 5 in which the reciprocating movement member is located in the second movement position P2, which is the normal observation position of the zoom lens 30, the operation member 52 is moved to the front L2 side from the states in FIG. 8 and FIG. 9. First, the operation member 52 transitions from the second state shown in FIG. 8 and FIG. 9 to the first state shown in FIG. 10 and FIG. 11.

At this point, as shown in FIG. 9 and FIG. 11, the first moving member 56 moves from the second position H2 to the first position H1, that is, fits in the linear section 70a from the key section 70b in the cam groove 70. The second moving member 58 stays in the third position H3.

The return member 52m biases the first biasing member 53 to the front L2 side and returns the first biasing member 53 to the first position H1. As a result, as shown in FIG. 10 and FIG. 11, a state in which the first biasing member 53 biases the reciprocating movement member 55 to the rear L1 side is released. The biasing is suppressed by the first switching member 57.

The second biasing member 54 keeps a state in which the biasing is suppressed by the second switching member 59. Therefore, even if the operation member 52 transitions from the second state to the first state, the reciprocating movement member 55 is not biased by the biasing member 54 and remains located in the first movement position P1 as shown in FIG. 10 and FIG. 11.

Thereafter, the operation member 52 is moved further to the front L2 side than in FIG. 10 and FIG. 11 to thereby transition from the first state shown in FIG. 10 and FIG. 11 to the third state shown in FIG. 4 and FIG. 5.

At this point, as shown in FIG. 11 and FIG. 5, the second moving member 58 moves from the third position H3 to the fourth position H4, that is, fits in the key section 70c from the linear section 70a in the cam groove 70. The first moving member 56 stays in the first position H1.

As a result, according to the fitting of the second moving member 58 in the key section 70c bending to the direction C2 side, as shown in FIG. 4 and FIG. 5, the second moving member 58 moves the spring section 54bs to the direction C2 side to a position where the spring section 54bs is not in contact with the protrusion 52b, whereby the second biasing member 54 biases the reciprocating movement member 55 to the front L2 side.

Therefore, the reciprocating movement member 55 moves from the first movement position P1 to the second movement position P2 and is pressed against the positioning protrusion 60a with a biasing force by the second biasing member 54. In this case, the first biasing member 53 keeps the state in which the biasing is suppressed by the first switching member 57.

Consequently, the operation member 52 transitions from the second state to the third state. The zoom lens 30 moves forward via the reciprocating movement member 55, the wire 51, and the zoom lens frame 31 to thereby move from the near point magnifying observation position to the normal observation position.

Contact sound of the reciprocating movement member 55 coming into contact with the positioning protrusion 60a or release sound of the biasing spring 54a released from the contracted state occurs. Therefore, the operator can easily recognize that the zoom lens 30 moves from the near point magnifying observation position to the normal observation position.

In this way, in the present embodiment, it is possible to switch the zoom lens 30 to the two positions of the normal observation position and the near point magnifying observation position and fix positions of the zoom lens 30 in the respective positions using the simple and small operation switching mechanism 50 configured by the wire 51, the operation member 52, the biasing members 53 and 54, the reciprocating movement member 55, and the switching members 57 and 59 configured as explained above.

Consequently, in the third state shown in FIG. 4 and FIG. 5 of the operation member 52 in which the reciprocating movement member 55 is located in the second movement position P2, which is the normal observation position of the zoom lens 30, the second biasing member 54 presses the reciprocating movement member 55 against the positioning protrusion 60a with a biasing force. Therefore, since constant tension can be always applied to the wire 51, it is possible to surely prevent unintended movement of the zoom lens 30 from the normal observation position due to, for example, intense operation of the endoscope 1.

Note that, by retaining the reciprocating movement member 55 in the first movement position P1 or the second movement position P2, it is possible to prevent the reciprocating movement member 55 from unintentionally colliding with the first biasing member 53 and the second biasing member 54 to release the respective biasing members or unnecessarily push in the wire 51.

In the second state shown in FIG. 8 and FIG. 9 of the operation member 52 in which the reciprocating movement member 55 is located in the first movement position P1, which is the near point magnifying observation position of the zoom lens 30, the first biasing member 53 presses the reciprocating movement member 55 against the positioning protrusion 60b with a biasing force. Therefore, since constant tension can be always applied to the wire 51, it is possible to surely prevent unintended movement of the zoom lens 30 from the near point magnifying observation position due to, for example, intense operation of the endoscope 1.

When the operation member 52 is moved from the third state shown in FIG. 4 and FIG. 5 in which the reciprocating movement member 55 is located in the second movement position P2, which is the normal observation position of the zoom lens 30, to the second state shown in FIG. 8 and FIG. 9 in which the reciprocating movement member 55 is located in the first movement position P1, which is the near point magnifying observation position, even if the operation member 52 passes the first state shown in FIG. 6 and FIG. 7, the reciprocating movement member 55 does not move from the second movement position P2 according to the suppression of the biasing by the first biasing member 53 by the first switching member 57 as shown in FIG. 6 and FIG. 7.

Further, when the operation member 52 is moved from the second state shown in FIG. 8 and FIG. 9 in which the reciprocating movement member 55 is located in the first movement position P1, which is the near point observation position, to the third state shown in FIG. 4 and FIG. 5 in which the reciprocating movement member 55 is located in the second movement position P2, which is the normal observation position of the zoom lens 30, even if the operation member 52 passes the first state shown in FIG. 10 and FIG. 11, the reciprocating movement member 55 does not move from the first movement position P1 according to the suppression of the biasing by the second biasing member 54 by the second switching member 59 as shown in FIG. 10 and FIG. 11.

That is, the reciprocating movement member 55 is not stopped and fixed in a halfway position in the longitudinal direction L between the normal observation position and the near point magnifying observation position and reciprocatingly moves to be switched to only the two positions of the normal observation position and the near point magnifying observation position. Positions of the reciprocating movement member 55 can be more surely fixed by the biasing members 53 and 54 in the respective positions.

The switching of the second state and the third state of the operation member 52, that is, the switching of the normal observation position and the near point magnifying observation position of the zoom lens 30 can be smoothly realized without a malfunction with a simple and small configuration in which the release of the suppression of the biasing by the first biasing member 53 involved in moving the first moving member 56 between the first position H1 and the second position H2 in the direction C using the cam groove 70 is used or the release of the suppression of the biasing by the second biasing member 54 involved in moving the second moving member 58 between the third position H3 and the fourth position H4 in the direction C using the cam groove 70 is used.

Further, the operation switching mechanism 50 in the present embodiment is configured from a linear switch including a simple mechanical configuration without using a shape memory alloy, a solenoid, or the like unlike in the past. Therefore, it is possible to realize the switching and movement of the two positions of the zoom lens 30 at low cost with a smaller configuration than in the past and without a malfunction.

The operation switching mechanism 50 is provided in the operation section 3. Therefore, it is possible to further reduce the insertion section 2 in diameter than when the operation switching mechanism 50 is provided in the insertion section 2 as in the past.

Consequently, it is possible to provide the operation switching mechanism 50 and the endoscope 1 that can realize, without a malfunction, surely and smoothly, and with a simple configuration, switching and fixing of the zoom lens 30 to two positions involved in reciprocating movement of the zoom lens 30 by the wire 51 while achieving a reduction in size.

(Second Embodiment)

Figure 13:
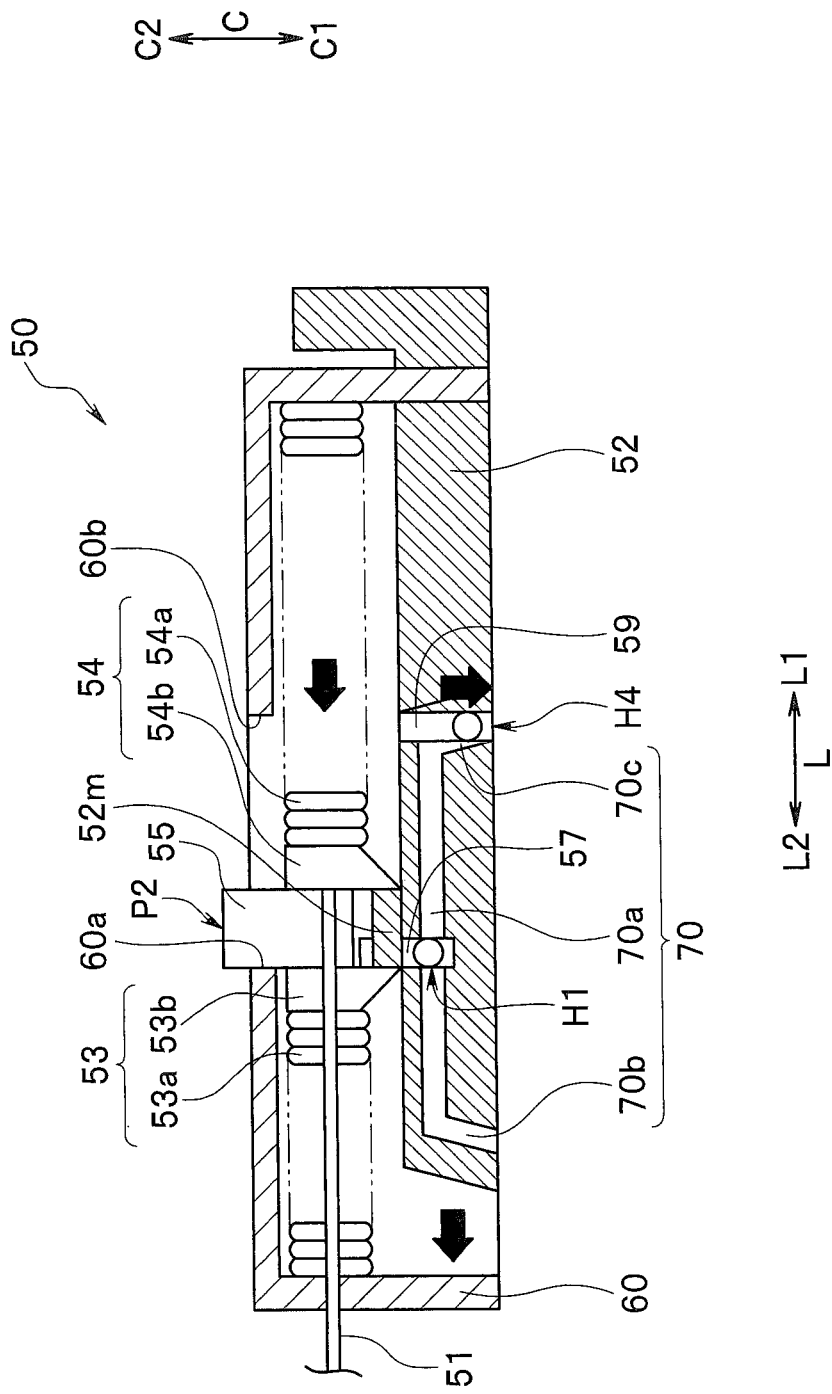
FIG. 13 is a partial sectional view of an operation switching mechanism schematically showing a third state of an operation member in the operation switching mechanism of a second embodiment and a state in which a reciprocating movement member is located in a second movement position.
Figure 14:
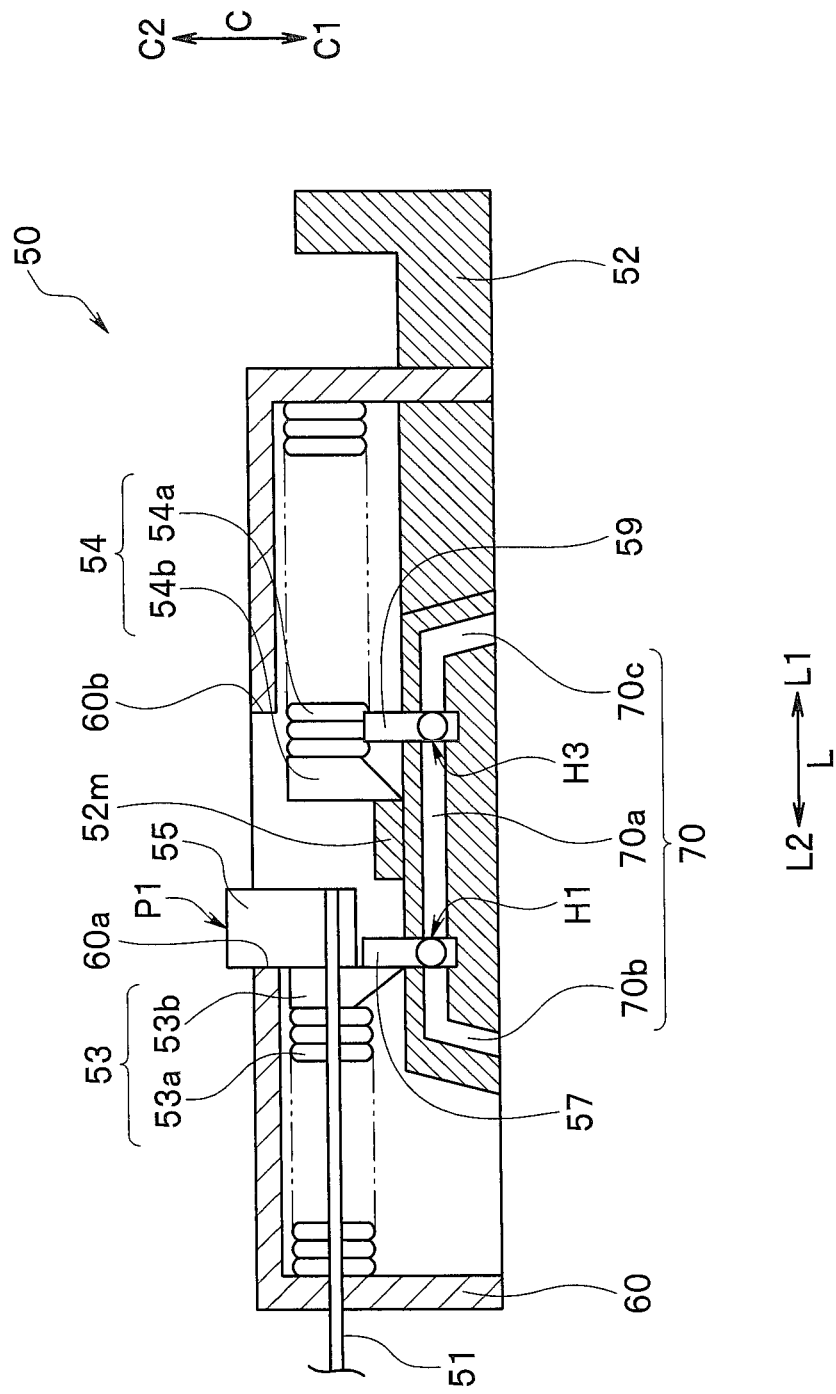
FIG. 14 is a partial sectional view of the operation switching mechanism schematically showing a first state of the operation member in the operation switching mechanism shown in FIG. 13 and the state in which the reciprocating movement member is located in the second movement position.

FIG. 13 is a partial sectional view of an operation switching mechanism schematically showing a third state of an operation member in the operation switching mechanism of a second embodiment and a state in which a reciprocating movement member is located in a second movement position. FIG. 14 is a partial sectional view of the operation switching mechanism schematically showing a first state of the operation member in the operation switching mechanism shown in FIG. 13 and the state in which the reciprocating movement member is located in the second movement position.

Figure 15:
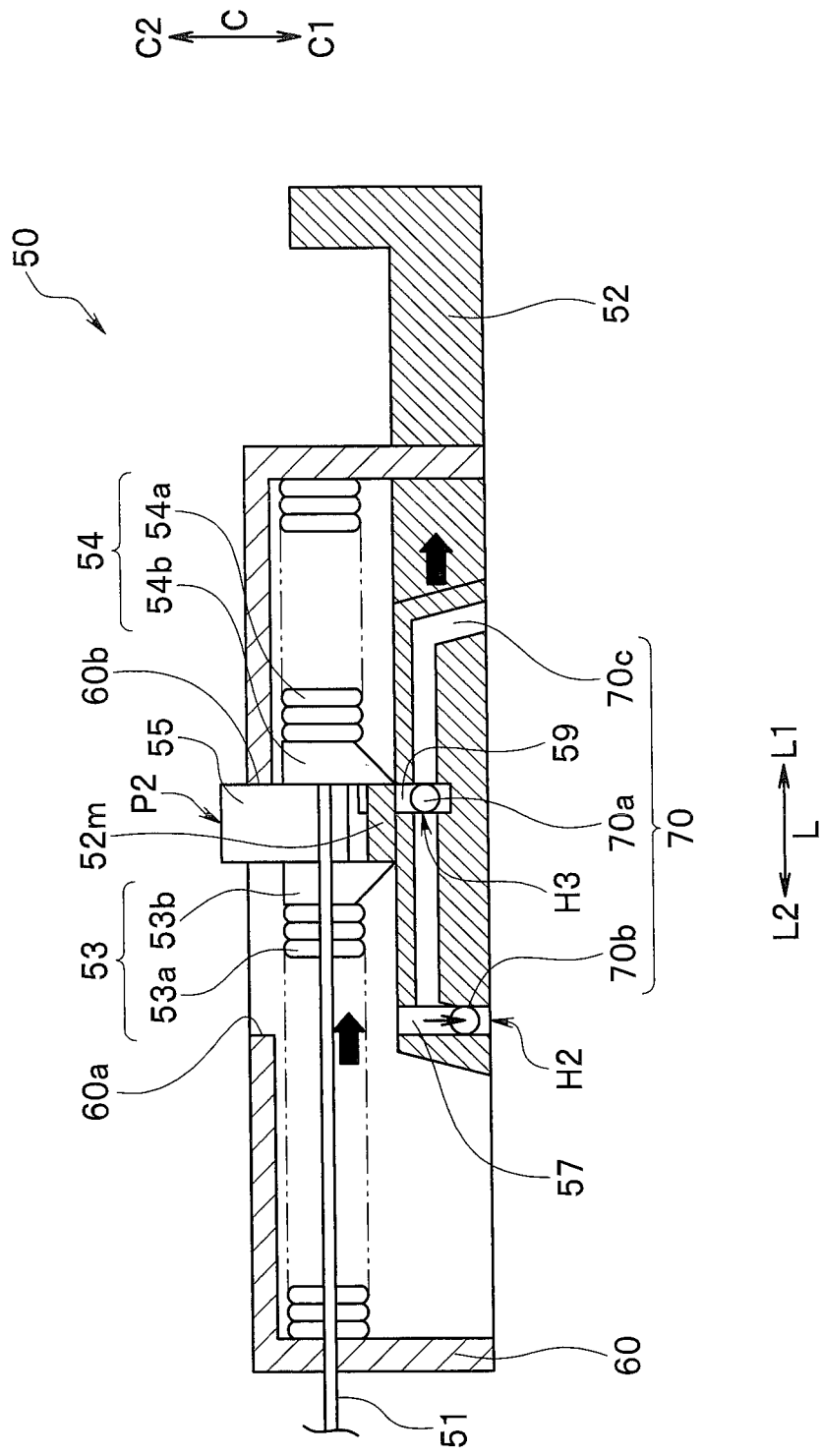
FIG. 15 is a partial sectional view of the operation switching mechanism schematically showing a second state of the operation member in the operation switching mechanism shown in FIG. 14 and a state in which the reciprocating movement member is located in a first movement position.
Figure 16:
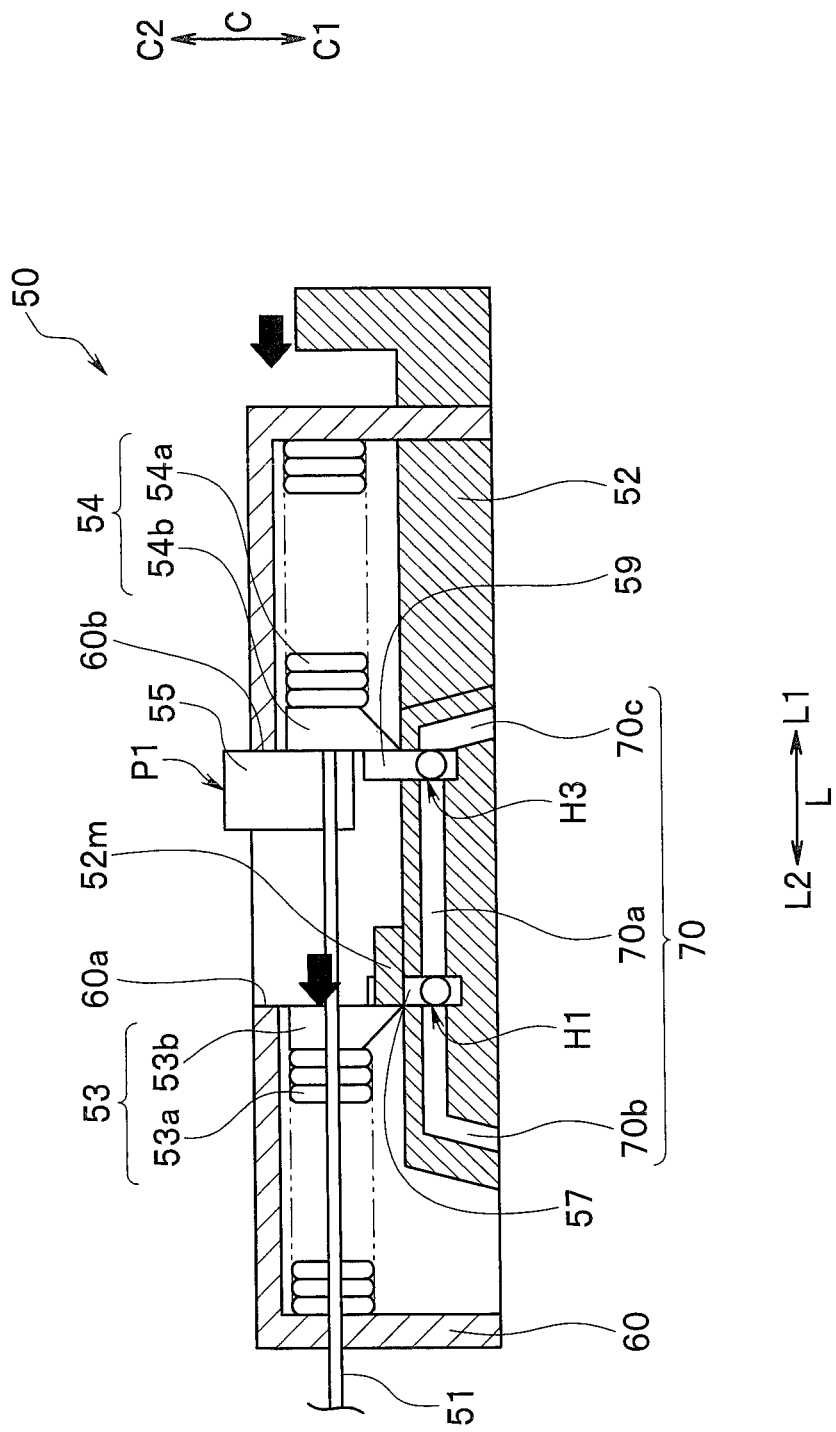
FIG. 16 is a partial sectional view of the operation switching mechanism schematically showing the first state of the operation member in the operation switching mechanism shown in FIG. 15 and the state in which the reciprocating movement member is located in the first movement position.

FIG. 15 is a partial sectional view of the operation switching mechanism schematically showing a second state of the operation member in the operation switching mechanism shown in FIG. 14 and a state in which the reciprocating movement member is located in a first movement position. FIG. 16 is a partial sectional view of the operation switching mechanism schematically showing the first state of the operation member in the operation switching mechanism shown in FIG. 15 and the state in which the reciprocating movement member is located in the first movement position.

A configuration of the operation switching mechanism of the second embodiment is different from the configuration of the operation switching mechanism in the first embodiment shown in FIG. 1 to FIG. 12 in that each of switching members is configured from one member and a formation direction of a key section in a groove of the operation member. Therefore, components same as the components in the first embodiment are denoted by the same reference numerals and signs and explanation of the components is omitted.

As shown in FIG. 13 to FIG. 16, in the present embodiment, each of the first switching member 57 and the second switching member 59 is configured from one member fit in the cam groove 70. Therefore, the first switching member 57 functions as the first moving member 56 as well and the second switching member 59 functions as the second moving member 58 as well.

In the present embodiment, the first switching member 57 and the second switching member 59 respectively come into contact with the pressing members 53b and 54b themselves in the first biasing member 53 and the second biasing member 54 to thereby suppress the biasing by the respective biasing members 53 and 54. Therefore, the pressing members 53b and 54b in the present embodiment do not respectively include the spring sections 53bs and 54bs.

In the present embodiment, the cam groove 70 includes the linear section 70a having a predetermined length along the longitudinal direction L, the key section 70b bending from a distal end of the linear section 70a to the direction C1 side, and the key section 70c bending from a proximal end of the linear section 70a to the direction C1 side.

Note that the other components are the same as the components of the first embodiment explained above.

Action of the operation switching mechanism 50 of the present embodiment configured in this way is explained.

First, in the operation member 52, when the reciprocating movement member 55 shown in FIG. 13 is located in the second movement position P2, which is the normal observation position of the zoom lens 30, as explained above, the first switching member 57 comes into contact with the pressing member 53b to suppress biasing by the first biasing member 53 and the second switching member 59 is not in contact with the pressing member 54b and releases suppression of biasing by the second biasing member 54. Therefore, according to the biasing to the front L2 side by the second biasing member 54, the reciprocating movement member 55 is pressed against the positioning protrusion 60a with a biasing force. The reciprocating movement member 55 less easily moves from the second movement position P2.

Thereafter, when the operation member 52 transitions from the third state in which the operation member 52 is located in the second movement position P2 to the second state shown in FIG. 15 in which the reciprocating movement member is located in the first movement position P1, which is the near point magnifying observation position of the zoom lens 30, the operation member 52 is moved to the rear L1 side from the state in FIG. 13. First, the operation member 52 transitions from the third state shown in FIG. 13 to the first state shown in FIG. 14.

At this point, as shown in FIG. 13 and FIG. 14, the second switching member 59 moves from the fourth position H4 to the third position H3, that is, fits in the linear section 70a from the key section 70c in the cam groove 70. The first switching member 57 stays in the first position H1.

The return member 52m biases the second biasing member 54 to the first movement position P1, that is, the rear L1 side and returns the second biasing member 54 to the third position H3. As a result, as shown in FIG. 14, a state in which the second biasing member 54 biases the reciprocating movement member 55 to the second movement position P2, that is, the front L2 side is released. The biasing is suppressed by the second switching member 59.

The first biasing member 53 keeps a state in which the biasing is suppressed by the first switching member 57. Therefore, even if the operation member 52 transitions from the third state to the first state, the reciprocating movement member 55 remains located in the second movement position P2 as shown in FIG. 14.

Thereafter, the operation member 52 is moved further to the rear L1 side than in FIG. 14 to thereby transition from the first state shown in FIG. 14 to the second state shown in FIG. 15.

At this point, as shown in FIG. 14 and FIG. 15, the first switching member 57 moves from the first position H1 to the second position H2, that is, fits in the key section 70b from the linear section 70a in the cam groove 70. The second switching member 59 stays in the third position H3.

As a result, as shown in FIG. 15, the suppression of the biasing by the first biasing member 53 by the first switching member 57 is released, whereby the first biasing member 53 biases the reciprocating movement member 55 to the rear L1 side.

Therefore, the reciprocating movement member 55 moves from the second movement position P2 to the first movement position P1 and is pressed against the positioning protrusion 60b with a biasing force by the first biasing member 53. In this case, the second biasing member 54 keeps the state in which the biasing is suppressed by the second switching member 59.

Consequently, the operation member 52 transitions from the third state to the second state. The zoom lens 30 moves backward via the reciprocating movement member 55, the wire 51, and the zoom lens frame 31 to thereby move from the normal observation position to the near point magnifying observation position.

Note that, since the key section 70b is bent as explained above, fitting sound occurs when the first switching member 57 fits in the key section 70b. Therefore, an operator can easily recognize that the zoom lens 30 moves from the normal observation position to the near point magnifying observation position.

In the operation member 52, when the reciprocating movement member 55 shown in FIG. 15 is located in the first movement position P1, which is the near point magnifying observation position of the zoom lens 30, as explained above, the second switching member 59 comes into contact with the pressing member 54b to thereby suppress the biasing by the second biasing member 54 and the first switching member 57 is not in contact with the pressing member 53b to release the suppression of the biasing by the first biasing member 53. Therefore, according to the biasing to the rear L1 side by the first biasing member 53, the reciprocating movement member 55 is pressed against the positioning protrusion 60b with a biasing force. Therefore, the reciprocating movement member 55 less easily moves from the first movement position P1.

Thereafter, when the operation member 52 transitions from the second state in which the operation member 52 is located in the first movement position P1 to the third state shown in FIG. 13 in which the reciprocating movement member is located in the second movement position P2, which is the normal observation position of the zoom lens 30, the operation member 52 is moved to the front L2 side from the state in FIG. 15. First, the operation member 52 transitions from the second state shown in FIG. 15 to the first state shown in FIG. 16.

At this point, as shown in FIG. 15 and FIG. 16, the first switching member 57 moves from the second position H2 to the first position H1, that is, fits in the linear section 70a from the key section 70b in the cam groove 70. The second switching member 59 stays in the third position H3.

The return member 52m biases the first biasing member 53 to the front L2 side and returns the first biasing member 53 to the first position H1. As a result, as shown in FIG. 16, a state in which the first biasing member 53 biases the reciprocating movement member 55 to the rear L1 side is released. The biasing is suppressed by the first switching member 57.

The second biasing member 54 keeps a state in which the biasing is suppressed by the second switching member 59. Therefore, even if the operation member 52 transitions from the second state to the first state, the reciprocating movement member 55 remains located in the first movement position P1 as shown in FIG. 16.

Thereafter, the operation member 52 is moved further to the front L2 side than in FIG. 16 to thereby transition from the first state shown in FIG. 16 to the third state shown in FIG. 13.

At this point, as shown in FIG. 16 and FIG. 13, the second switching member 59 moves from the third position H3 to the fourth position H4, that is, fits in the key section 70c from the linear section 70a in the cam groove 70. The first switching member 57 stays in the first position H1.

As a result, as shown in FIG. 13, the second switching member 59 releases the suppression of the biasing by the second biasing member 54, whereby the second biasing member 54 biases the reciprocating movement member 55 to the front L2 side. Therefore, the reciprocating movement member 55 moves from the first movement position P1 to the second movement position P2 and is pressed against the positioning protrusion 60a with a biasing force by the second biasing member 54. In this case, the first biasing member 53 keeps a state in which the biasing is suppressed by the first switching member 57.

Consequently, the operation member 52 transitions from the second state to the third state. The zoom lens 30 moves forward via the reciprocating movement member 55, the wire 51, and the zoom lens frame 31 to thereby move from the near point magnifying observation position to the normal observation position.

Note that, since the key section 70c is bent as explained above, fitting sound occurs when the switching member 59 fits in the key section 70c. Therefore, the operator can easily recognize that the zoom lens 30 moves from the near point magnifying observation position to the normal observation position.

Note that other action is the same as the action in the first embodiment explained above.

According to the present embodiment explained above, it is possible to obtain an effect same as the effect in the first embodiment.

Figure 17:
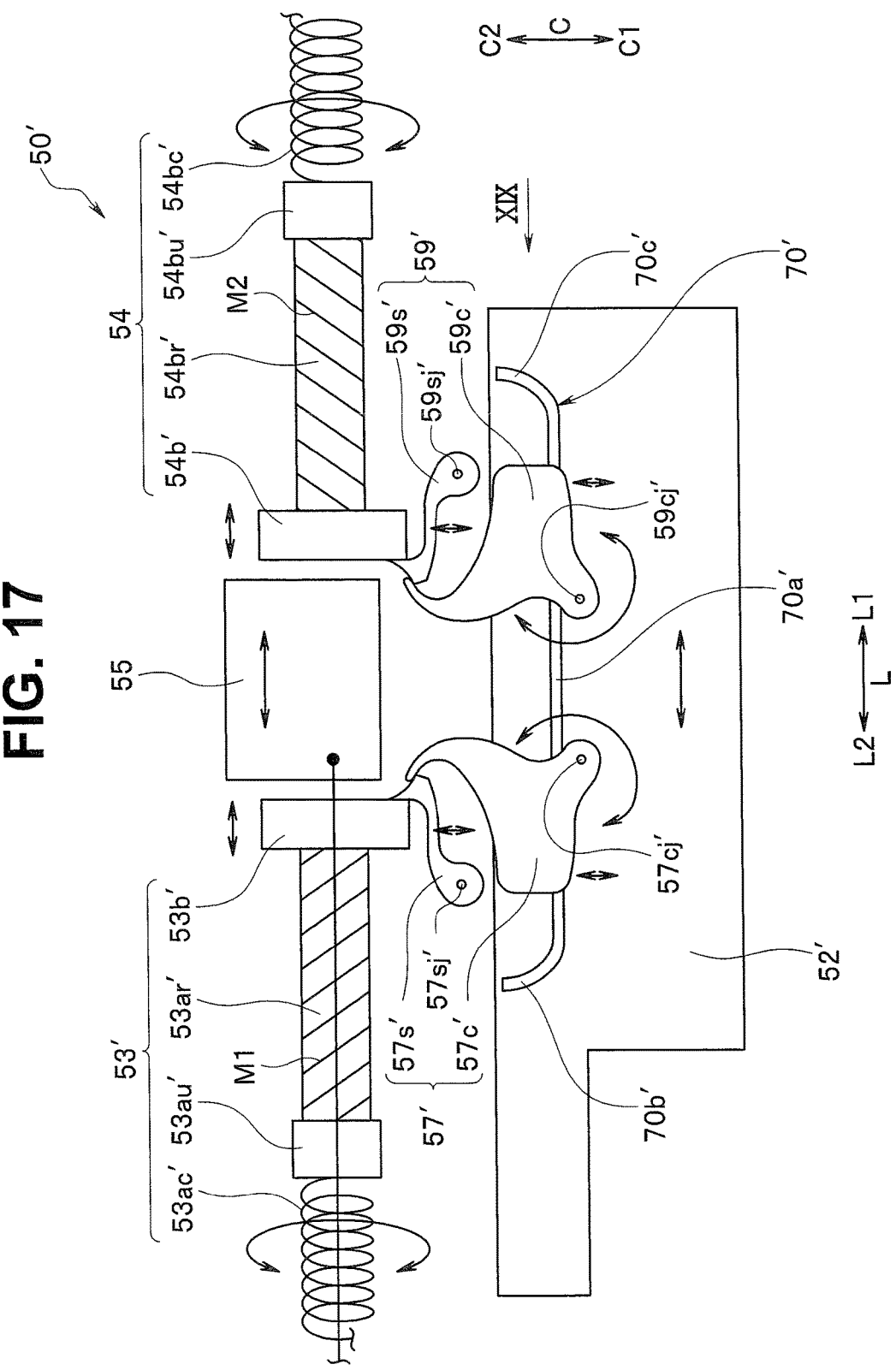
FIG. 17 is a diagram schematically showing another configuration of the operation switching mechanism different from the configurations in FIG. 1 to FIG. 16.
Figure 18:
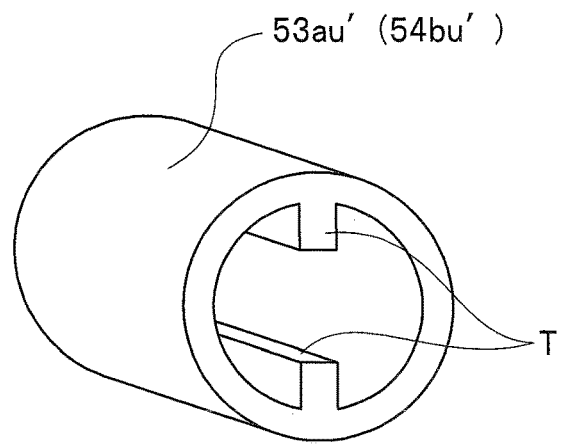
FIG. 18 is a perspective view enlarging and showing a spiral-groove fitting member shown in FIG. 17.
Figure 19:
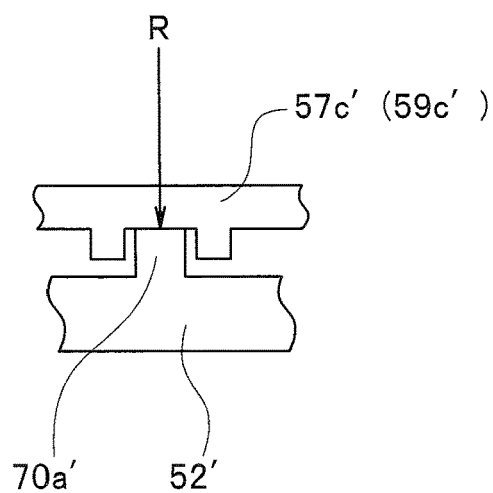
FIG. 19 is a diagram of a fitting state of a cam and the operation member shown in FIG. 17 viewed from a XIX direction in FIG. 17.

Note that a modification is explained below with reference to FIG. 17 to FIG. 19. FIG. 17 is a diagram schematically showing another configuration of the operation switching mechanism different from the configurations in FIG. 1 to FIG. 16. FIG. 18 is a perspective view enlarging and showing a spiral-groove fitting member shown in FIG. 17. FIG. 19 is a diagram of a fitting state of the cam and the operation member shown in FIG. 17 viewed from a XIX direction in FIG. 17.

As shown in FIG. 17, a first biasing member 53' in an operation switching mechanism 50' may be configured from a torsion coil 53ac', a spiral-groove fitting member 53au' provided at one end of the torsion coil 53ac', a spiral bar 53ar' including a spiral groove M1 in which a protrusion T of the groove fitting member 53au' fits as shown in FIG. 18, and a pressing member 53b'.

A second biasing member 54' may be configured from a torsion coil 54ac', a spiral-groove fitting member 54au' provided at one end of the torsion coil 54ac', a spiral bar 54ar' including a spiral groove M2 in which a protrusion T of the groove fitting member 54au' fits as shown in FIG. 18, and a pressing member 54b'.

With such configurations of the biasing members 53' and 54', according to turning, the protrusions T respectively move in the spiral grooves M1 and M2, whereby the respective biasing members 53' and 54' respectively bias the reciprocating movement member 55 to the first movement position P1, that is, the rear L1 side, and the second movement position P2, that is, the front L2 side, in the longitudinal direction L.

Further, as shown in FIG. 17, a first switching member 57' may be configured from a stopper 57s' and a cam member 57c'. A second switching member 59' may be configured from a stopper 59s' and a cam member 59c'.

The stopper 57s' is capable of turning around a turning axis 57sj'. Therefore, the stopper 57s' is capable of moving to the first position H1 and the second position H2 in the direction C. The stopper 57s' comes into contact with the pressing member 53b' in the first position H1 to thereby suppress biasing by the first biasing member 53'. The stopper 57s' is not in contact with the pressing member 53b' in the second position H2 to thereby release the suppression of the biasing by the first biasing member 53'.

The stopper 59s' is capable of turning around a turning axis 59sj'. Therefore, the stopper 59s' is capable of moving to the third position H3 and the fourth position H4 in the direction C. The stopper 59s' comes into contact with the pressing member 54b' in the third position 113 to thereby suppress biasing by the second biasing member 54'. The stopper 59s' is not in contact with the pressing member 54b' in the fourth position H4 to thereby release the suppression of the biasing by the second biasing member 54'.

The cam members 57c' and 59' are capable of turning around the respective turning axes 57cj' and 59cj'. As shown in FIG. 19, the cam members 57c' and 59' include a groove R that fits with a convex rail 70' provided in the operation member 52'.

The rail 70' includes a linear section 70a' having a predetermined length along the longitudinal direction L, a key section 70b' bending from a distal end of the linear section 70a' to the direction C2 side, and a key section 70c' bending from a proximal end of the linear section 70a to the direction C2 side.

The cam member 57c' has a function of, in a state in which the groove R fits with the linear section 70a', being caught by the stopper 57s', fixing the stopper 57s' in the first position H1 where the stopper 57s' is in contact with the pressing member 53b', according to movement of the operation member 52' to the rear L1 side, fitting in the key section 70b' to thereby rotate clockwise, releasing locking of the stopper 57s', moving the stopper 57s' from the first position H1 to the second position H2, and, according to movement of the operation member 52' to the front L2 side, fitting in the linear section 70a' to thereby push up the stopper 57s' to be locked to the stopper 57s', and moving the stopper 57s' from the second position H2 to the first position H1.

The cam member 59c' has a function of, in the state in which the groove R fits with the linear section 70a', being caught by the stopper 59s', fixing the stopper 59s' in the third position H3 where the stopper 59s' is in contact with the pressing member 54b', according to movement of the operation member 52' to the front L2 side, fitting in the key section 70c' to thereby rotate counterclockwise, releasing locking of the stopper 59s', moving the stopper 59s' from the third position H3 to the fourth position H4, and, according to movement of the operation member 52' to the rear L1 side, fitting in the linear section 70a' to thereby push up the stopper 59s' to be locked to the stopper 59s', and moving the stopper 59s' from the fourth position H4 to the third position H3.

With such a configuration of the operation switching mechanism 50', it is possible to obtain an effect same as the effect of the operation switching mechanism 50 of the first and second embodiments.

Another modification is explained below. In the first and second embodiments, the first movement position P1 of the reciprocating movement member 55 is explained as being the near point magnifying observation position and the second movement position P2 is explained as being the normal observation position. However, the first movement position P1 and the second movement position P2 are not limited thereto and naturally may be other positions of an optical system.

In the first and second embodiments, the operating section is explained as being the zoom lens 30. The operation switching mechanism 50 is explained as performing the switching and fixing of the two positions of the zoom lens 30. However, the operation switching mechanism 50 is not limited to this and is also applicable in, as long as two values can be switched using a long member and positions of the two values can be fixed, a configuration for switching another operating section to two positions and moving the operation section, for example, a configuration for surely switching actually bending length of the bending section 2w provided in the insertion section 2 of the endoscope 1 to either one of two lengths and a configuration for switching, in a binary manner, a position of a filter that imparts an optical effect to various optical systems provided at the distal end portion 2s of the insertion section 2.

The operation switching mechanism 50 is also applicable in, for example, a configuration for switching a bending length of the bending section 2w in two stages according to movement of the long member and a configuration for switching hardness of the flexible tube section 2k to two kinds of hardness according to the movement of the long member and the like.

Further, in the first and second embodiments explained above, the example is explained in which the switching member is configured from the two members, that is, the first switching member 57 and the second switching member 59. However, the switching member is not limited to this and may be configured from one member.

In this case, the switching member only has to include, for example, a seesaw mechanism that swings around a fulcrum and switch the suppression of the biasing by the first biasing member 53 and the release of the suppression of the biasing by the second biasing member 54 and the release of the suppression of the biasing by the first biasing member 53 and the suppression of the biasing by the second biasing member 54.

Further, the respective embodiments may be used in a normal endoscope of a single screen type including one system of an optical system that observes an inside of a subject.

Figure 20:
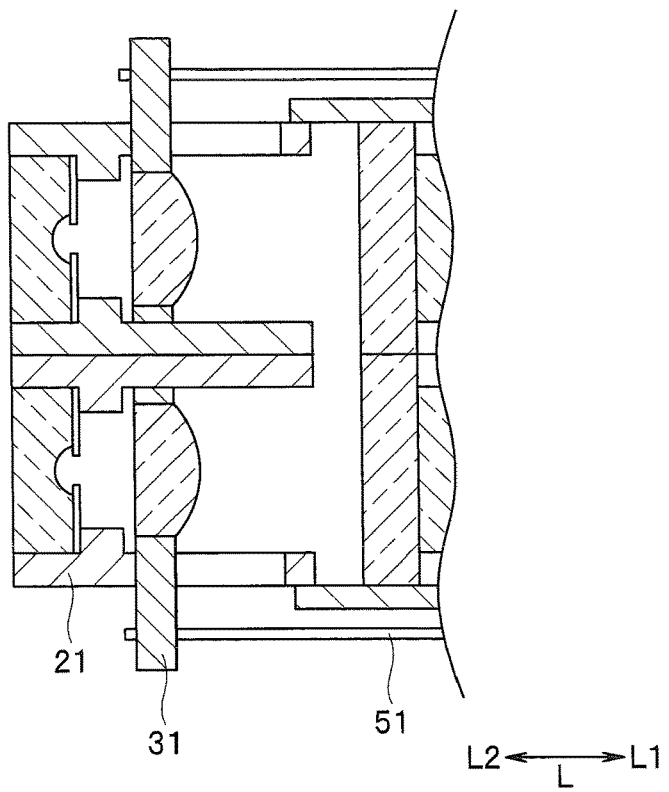
FIG. 20 is a partial sectional view showing a modification in which the optical system shown in FIG. 2B is configured from two optical systems.
Figure 21:
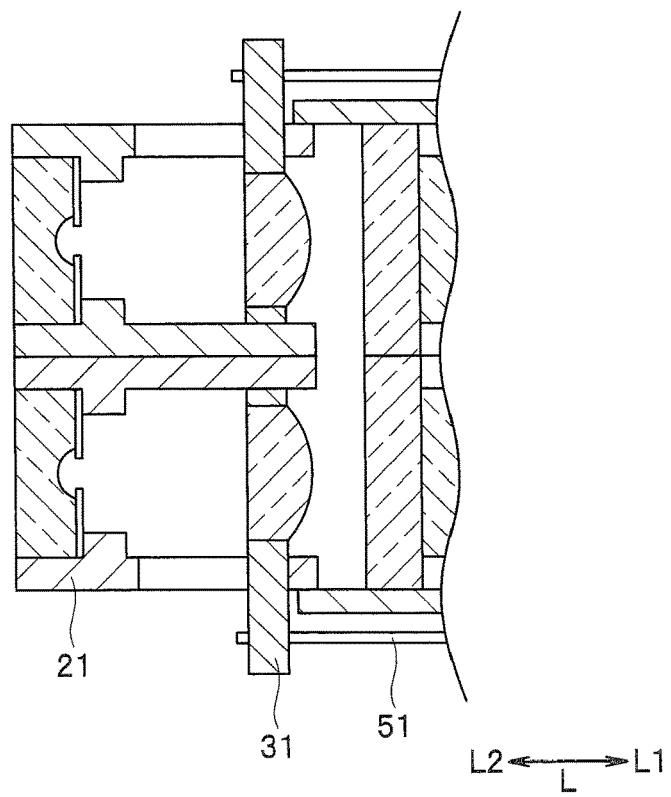
FIG. 21 is a partial sectional view showing a modification in which the optical system shown in FIG. 2C is configured from two optical systems.

FIG. 20 is a partial sectional view showing a modification in which the optical system shown in FIG. 2B is configured from two optical systems. FIG. 21 is a partial sectional view showing a modification in which the optical system shown in FIG. 2C is configured from two optical systems.

For example, as shown in FIG. 20 and FIG. 21, the embodiments can also be used in a stereoscopic observation endoscope that performs three-dimensional observation by obtaining an image of an inside of a subject with a plurality of, for example, two optical systems.

In such a case, the plurality of, for example, two optical systems may be able to be switched by one operation switching mechanism. The respective optical systems may be able to be switched by individual operation switching mechanisms.

Such an endoscope has an observation position suitable for three-dimensional observation. Therefore, the operation switching mechanisms of the respective embodiments may be used such that the endoscope can be appropriately switched to a necessary observation position suitable in performing the three-dimensional observation.

What is claimed is:
1. An operation switching mechanism comprising:
an elongated member configured to transmit a force for operating an operating section;
a movement member to which the elongated member is connected, the movement member moving between a first movement position and a second movement position together with the elongated member;
a first biasing member configured to bias the movement member toward the first movement position;
a second biasing member configured to bias the movement member toward the second movement position on an opposite side to a side that the first biasing member biases the movement member;
a switching member including:
a first switching member configured to switch between suppression of biasing by the first biasing member and release of the suppression of the biasing by the first biasing member, and
a second switching member configured to switch between suppression of biasing by the second biasing member and release of the suppression of the biasing by the second biasing member,
wherein the switching member is configured to switch to one of the suppression of the biasing by the first biasing member by the first switching member, the suppression of the biasing by the second biasing member by the second switching member, and suppression of biasing by both of the first biasing member and the second biasing member by the first switching member and the second switching member, respectively; and
an operation member configured to operate the switching member and move the movement member to the first movement position or to the second movement position, wherein
the first biasing member includes a first biasing spring and a first pressing member, the first pressing member being provided to the first biasing spring, configured to press the movement member, and including a first deformation portion,
the second biasing member includes a second biasing spring and a second pressing member, the second pressing member being provided to the second biasing spring, configured to press the movement member, and including a second deformation portion,
the first switching member includes a first protrusion and a first movement member, wherein the first movement member is configured to move in a direction crossing a longitudinal direction of the elongated member between a first position at which the first protrusion comes into contact with the first pressing member to suppress the biasing by the first biasing spring and a second position at which the first deformation portion is deformed to release the contact of the first protrusion with the first pressing member to thereby release the suppression of the biasing by the first biasing member, and
the second switching member includes a second protrusion and a second movement member, wherein the second movement member is configured to move in the direction crossing the longitudinal direction of the elongated member between a third position at which the second protrusion comes into contact with the second pressing member to suppress the biasing by the second biasing spring and a fourth position at which the second deformation portion is deformed to release the contact of the second protrusion with the second press- ing member to thereby release the suppression of the biasing by the second biasing member.

2. The operation switching mechanism according to claim 1, wherein the switching member performs an operation for switching from a first configuration defined by suppression of the biasing by the first biasing member and release of suppression of the biasing by the second biasing member to a second configuration defined by suppression of the biasing by the second biasing member and release of suppression of the biasing by the first biasing member.

3. The operation switching mechanism according to claim 1, wherein the switching member performs, after performing the suppression of the biasing by the first biasing member and the suppression of the biasing by the second biasing member, an operation of switching between a state of releasing the suppression of the biasing by the second biasing member while still suppressing the biasing by the first biasing member and a state of releasing the suppression of the biasing by the first biasing member while keeping suppressing the biasing by the second biasing member.

4. The operation switching mechanism according to claim 1, wherein the operation member moves the first moving member between the first position and the second position or moves the second moving member between the third position and the fourth position.

5. The operation switching mechanism according to claim 4, wherein the operation member switches to any one state of
   a first state in which the operation member disposes the first moving member in the first position and disposes the second moving member in the third position to thereby arrange the movement member in the first movement position or the second movement position,
   a second state in which the operation member disposes the first moving member in the second position and disposes the second moving member in the third position to thereby arrange the movement member in the first movement position according to biasing to the one side by the first biasing member, and
   a third state in which the operation member disposes the first moving member in the first position and disposes the second moving member in the fourth position to thereby arrange the movement member in the second movement position according to biasing to another side by the second biasing member.

6. The operation switching mechanism according to claim 5, wherein, when the operation member transitions from the first state to the second state, the first moving member moves from the first position to the second position, the second moving member stays in the third position, the first biasing member biases the movement member to the one side in the longitudinal direction, and the second biasing member keeps a state in which the biasing is suppressed by the second switching member.

7. The operation switching mechanism according to claim 5, wherein, when the operation member transitions from the second state to the first state, the first moving member moves from the second position to the first position, the second moving member stays in the third position, a state in which the first biasing member biases the movement member to the one side in the longitudinal direction is released, the biasing by the first biasing member is suppressed by the first switching member, and the second biasing member keeps a state in which the biasing is suppressed by the second switching member.

8. The operation switching mechanism according to claim 5, wherein, when the operation member transitions from the first state to the third state, the second moving member moves from the third position to the fourth position, the first moving member stays in the first position, the second biasing member biases the movement member to the other side in the longitudinal direction, and the first biasing member keeps a state in which the biasing is suppressed by the first switching member.

9. The operation switching mechanism according to claim 5, wherein, when the operation member transitions from the third state to the first state, the second moving member moves from the fourth position to the third position, the first moving member stays in the first position, a state in which the second biasing member biases the movement member to the other side in the longitudinal direction is released, the biasing by the second biasing member is suppressed by the second switching member, and the first biasing member keeps a state in which the biasing is suppressed by the first switching member.

10. The operation switching mechanism according to claim 1, further comprising a resisting section provided in at least one of the reciprocating movement member or the elongated member and configured to apply a resistance force against the reciprocating movement member moving from the first movement position or the second movement position in the longitudinal direction of the elongated member with a force equal to or larger than a biasing force of the first biasing member or a biasing force of the second biasing member.

11. An endoscope comprising:
   an insertion section inserted into a subject;
   the operating section provided in the insertion section; and
   the operation switching mechanism according to claim 1 configured to switch an operation state of the operating section.

12. The endoscope according to claim 11, wherein the operating section is an optical member of an optical system for observing an inside of the subject, and the elongated member moves the optical member to thereby adjust optical characteristics of the optical system.

13. The endoscope according to claim 11, wherein
   the operating section is a plurality of optical members of a plurality of optical systems to perform three-dimensional observation of an inside of the subject, and
   the elongated member moves the respective optical members to thereby adjust optical characteristics of the optical systems to change to a state in which the three-dimensional observation can be performed.

* * * * *